(12) United States Patent
Roudier et al.

(10) Patent No.: US 8,338,188 B2
(45) Date of Patent: Dec. 25, 2012

(54) METHODS AND KITS FOR THE DIAGNOSIS OF RHEUMATOID ARTHRITIS

(75) Inventors: Jean Roudier, Marseille Cedex (FR); Isabelle Auger, Marseille Cedex (FR)

(73) Assignee: Inserm (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 12/989,806

(22) PCT Filed: May 12, 2009

(86) PCT No.: PCT/EP2009/055731
§ 371 (c)(1),
(2), (4) Date: Nov. 23, 2010

(87) PCT Pub. No.: WO2009/138408
PCT Pub. Date: Nov. 19, 2009

(65) Prior Publication Data
US 2011/0065609 A1    Mar. 17, 2011

(30) Foreign Application Priority Data

May 14, 2008    (EP) ..................................... 08305167

(51) Int. Cl.
*G01N 33/564* (2006.01)
(52) U.S. Cl. ......... 436/509; 435/7.1; 436/506; 436/507; 436/508
(58) Field of Classification Search ........... 436/506–509
See application file for complete search history.

(56) References Cited

PUBLICATIONS

Fensterle et al., B-Raf specific antibody responses in melanoma patients, Sep. 2004, BMC Cancer, vol. 4, Ed. 62, pp. 1-9.*
Harlow, E. and Lane, D., Antibodies: A Laboratory Manual, 1988, Cold Spring Harbor Laboratory Press, Cold Spring Harbor, NY, pp. 23-26.*
Lederman et al., A single amino acid substitution in a common African allele of the CD4 molecule ablates binding of the monoclonal antibody, OKT4, 1991, Mol Immunol., vol. 28, No. 11, pp. 1171-1181.*
Colman, P.M., Effects of amino acid sequence changes on antibody-antigen interactions, 1994, Research in Immunology, vol. 145, No. 1, pp. 33-36.*
Burgess et al., Possible dissociation of the heparin-binding and mitogenic activities of heparin-binding (acidic fibroblast) growth factor-1 from its receptor-binding activities by site-directed mutagenesis of a single lysine residue, 1990, The Journal of Cell Biology, vol. 111, pp. 2129-2138.*

(Continued)

*Primary Examiner* — Melanie J Yu
*Assistant Examiner* — Erik B Crawford
(74) *Attorney, Agent, or Firm* — McAndrews, Held & Malloy Ltd.

(57) ABSTRACT

The present invention relates to the identification and use of proteins with clinical relevance to rheumatoid arthritis (RA). In particular, the invention provides the identity of marker proteins that specifically react with RA-associated autoantibodies. Also provided are methods, arrays and kits for using these proteins in the diagnosis of RA, and in the selection and/or monitoring of treatment regimens.

7 Claims, 8 Drawing Sheets

PUBLICATIONS

Tao, M. and Morrison, S.L., Studes of aglycosylated chimeric mouse-human IgG: Role of carbohydrate in the structure and effector functions mediated by the human IgG constant region, 1989, The Journal of Immunology, vol. 143, No. 8, pp. 2595-2601.*

Lazar et al., Transforming growth factor alpha: Mutation of aspartic acid 47 and leucine 48 results in different biological activities, 1988, Molecular and Cellular Biology, vol. 8, No. 3, pp. 1247-1252.*

International Search Report in PCT/EP09/55731, dated Nov. 4, 2009.

de Vries-Bouwstra et al., Arthritis and Rheumatism, 58(5):1293-1298 (2008).

Fensterle et al., BMC Cancer, 4(1):62 (2004).

Kim et al., Clin. Endocrin., 65(3):364-368 (2006).

Suzuki et al., Nat. Genet., 34(4):395-402 (2003).

* cited by examiner

| Proteins | Number of patients positive for the proteins | | | | | GenBank Accession Number |
|---|---|---|---|---|---|---|
| | RA (19) | AS (7) | SLE (2) | SSC (4) | Healthy controls (10) | |
| PAD4 | 9 | 0 | 0 | 0 | 0 | NM_012387.1 |
| BRAF catalytic domain | 9 | 0 | 0 | 0 | 1 | NM_004333.1 |
| Tumor suppressing subtransferable candidate 4 | 7 | 1 | 0 | 1 | 1 | BC050616.1 |
| Protein kinase C beta 1 | 6 | 0 | 0 | 0 | 0 | NM_212535 |
| Nucleoside diphosphate linked moiety X type motif 21 | 6 | 0 | 0 | 1 | 1 | NM_007006.1 |
| EPH receptor B1 | 5 | 1 | 0 | 1 | 0 | NM_004441.3 |
| Microtubule associated RP EB family member | 5 | 1 | 0 | 1 | 0 | NM_014268.1 |
| PIP4K2C | 5 | 0 | 0 | 0 | 0 | NM_024779.2 |
| Protein kinase C theta | 5 | 0 | 0 | 0 | 1 | NM_006257 |
| V ERB B2 | 4 | 1 | 0 | 0 | 0 | NM_001005862 |
| Calcium calmodulin dependent protein kinase II alpha | 4 | 0 | 0 | 1 | 0 | NM_015981 |
| Protein kinase C alpha | 4 | 1 | 0 | 0 | 1 | NM_002737 |
| Protein kinase C beta 1 | 4 | 1 | 0 | 0 | 1 | NM_002738 |
| DEP domain 6 | 4 | 0 | 0 | 1 | 1 | BC012040.1 |

Figure 4

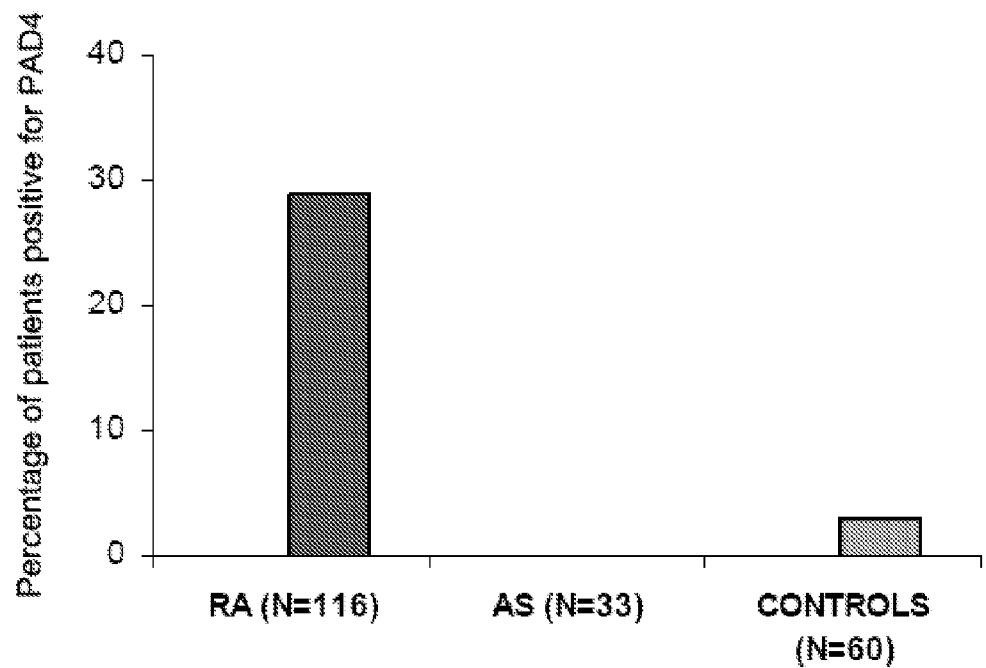
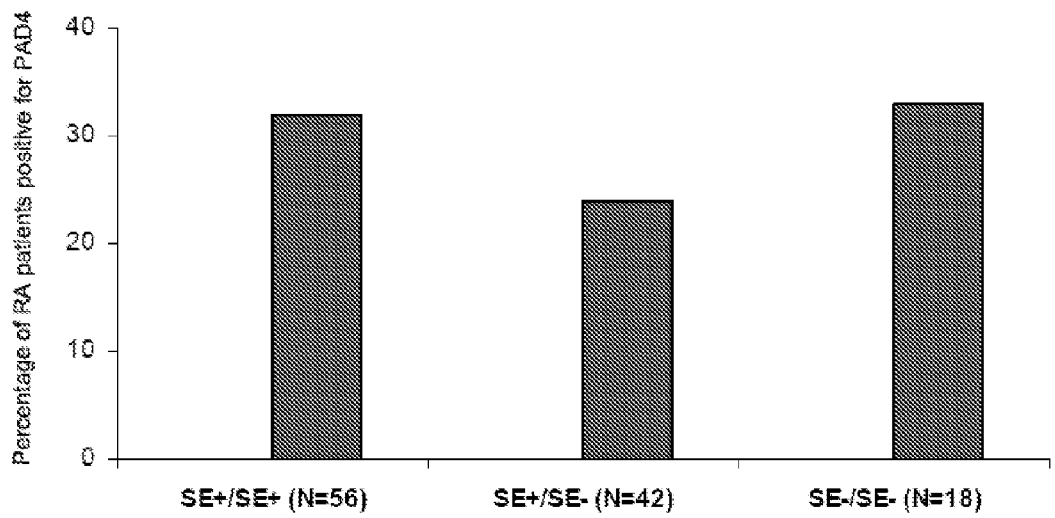
Figure 5

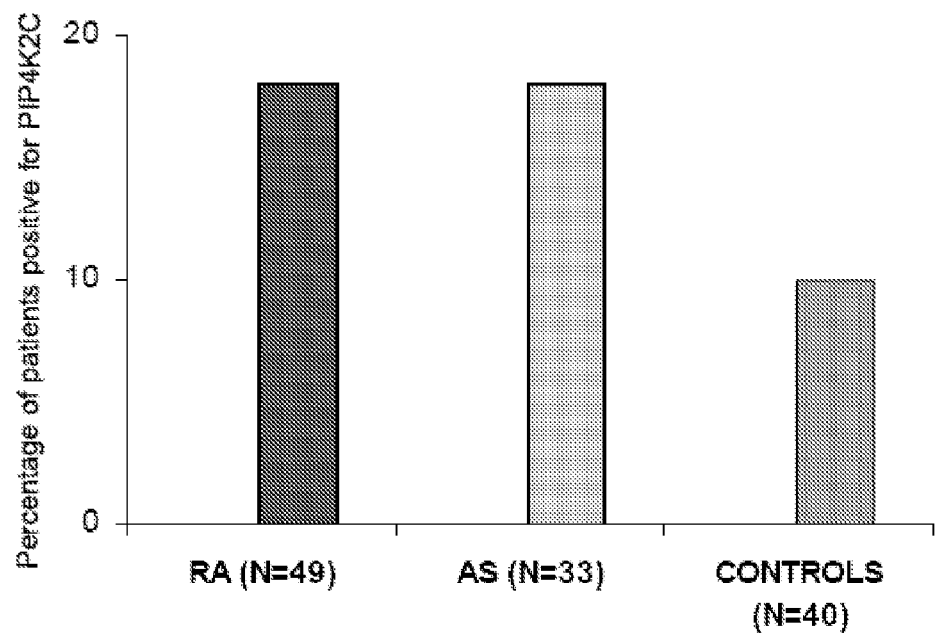
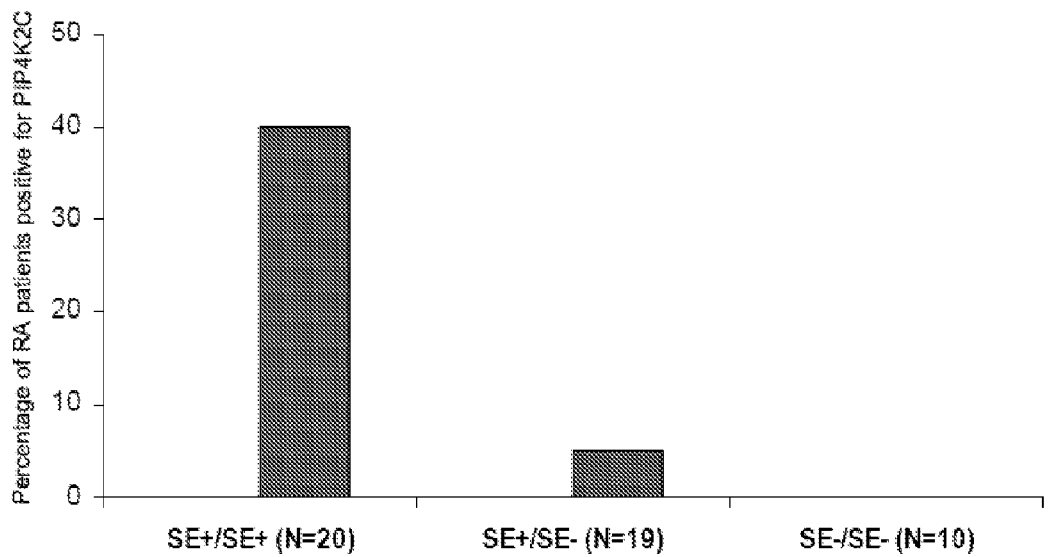
Figure 6

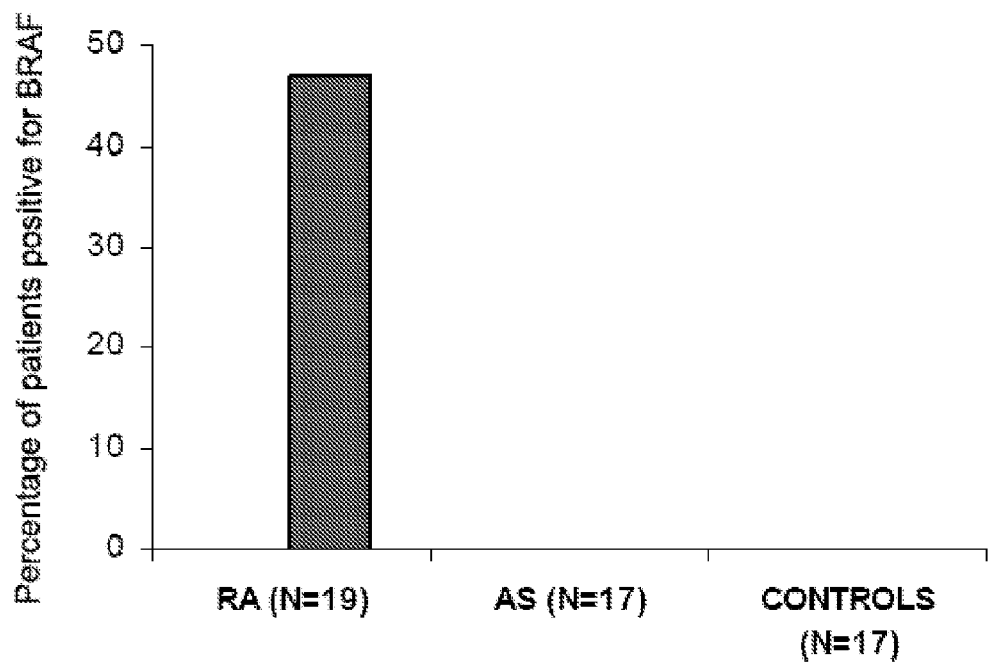
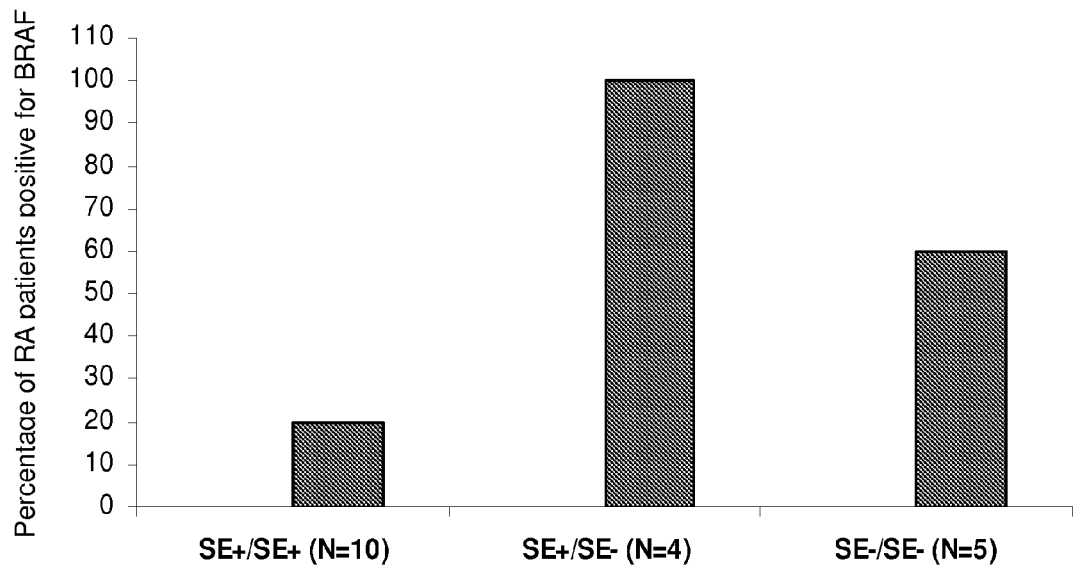
Figure 7

SEQUENCE LISTING

```
<160> NUMBER OF SEQ ID NOS: 3

<210> SEQ ID NO 1
<211> LENGTH: 766
<212> TYPE: PRT
<213> ORGANISM: Homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
                100                 105                 110

Ser Ser Ala Ser Met Asp Thr Val Thr Ser Ser Ser Ser Ser Ser Leu
            115                 120                 125

Ser Val Leu Pro Ser Ser Leu Ser Val Phe Gln Asn Pro Thr Asp Val
    130                 135                 140
```

```
Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
            165                 170                 175

Val Arg Asp Ser Leu Lys Lys Ala Leu Met Met Arg Gly Leu Ile Pro
        180                 185                 190

Glu Cys Cys Ala Val Tyr Arg Ile Gln Asp Gly Glu Lys Lys Pro Ile
    195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575
```

```
Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
            690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
            755                 760                 765

<210> SEQ ID NO 2
<211> LENGTH: 766
<212> TYPE: PRT
<213> ORGANISM: Homo sapiens

<400> SEQUENCE: 2

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
            115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190
```

-continued

```
Glu Cys Cys Ala Val Tyr Arg Ile Gln Asp Gly Lys Lys Pro Ile
            195                 200                 205
Gly Trp Asp Thr Asp Ile Ser Trp Leu Thr Gly Glu Glu Leu His Val
    210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
            260                 265                 270
Ser Thr Glu Val Pro Leu Met Cys Val Asn Tyr Asp Gln Leu Asp Leu
        275                 280                 285
Leu Phe Val Ser Lys Phe Phe Glu His His Pro Ile Pro Gln Glu Glu
    290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
                325                 330                 335
Ser Lys Ser Ile Pro Ile Pro Gln Pro Phe Arg Pro Ala Asp Glu Asp
            340                 345                 350
His Arg Asn Gln Phe Gly Gln Arg Asp Arg Ser Ser Ala Pro Asn
        355                 360                 365
Val His Ile Asn Thr Ile Glu Pro Val Asn Ile Asp Asp Leu Ile Arg
    370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
            420                 425                 430
Glu Asp Arg Asn Arg Met Lys Thr Leu Gly Arg Arg Asp Ser Ser Asp
        435                 440                 445
Asp Trp Glu Ile Pro Asp Gly Gln Ile Thr Val Gly Gln Arg Ile Gly
    450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
        515                 520                 525
Thr Gln Trp Cys Glu Gly Ser Ser Leu Tyr His His Leu His Ile Ile
    530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
                565                 570                 575
Leu Lys Ser Asn Asn Ile Phe Leu His Glu Asp Leu Thr Val Lys Ile
            580                 585                 590
Gly Asp Phe Gly Leu Ala Thr Glu Lys Ser Arg Trp Ser Gly Ser His
        595                 600                 605
Gln Phe Glu Gln Leu Ser Gly Ser Ile Leu Trp Met Ala Pro Glu Val
    610                 615                 620
```

```
Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His
                755                 760                 765

<210> SEQ ID NO 3
<211> LENGTH: 663
<212> TYPE: PRT
<213> ORGANISM: Homo sapiens

<400> SEQUENCE: 3

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Ser Pro Pro Ala Lys Lys Lys Ser Thr Gly
        50                  55                  60

Ser Ser Thr Trp Pro Leu Asp Pro Gly Val Glu Val Thr Leu Thr Met
65                  70                  75                  80

Lys Ala Ala Ser Gly Ser Thr Gly Asp Gln Lys Val Gln Ile Ser Tyr
                85                  90                  95

Tyr Gly Pro Lys Thr Pro Val Lys Ala Leu Leu Tyr Leu Thr Ala
                100                 105                 110

Val Glu Ile Ser Leu Cys Ala Asp Ile Thr Arg Thr Gly Lys Val Lys
            115                 120                 125

Pro Thr Arg Ala Val Lys Asp Gln Arg Thr Trp Thr Trp Gly Pro Cys
130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240
```

-continued

Pro Gly Gly Lys His Asn Met Asp Phe Tyr Val Glu Ala Leu Ala Phe
            245                 250                 255

Pro Asp Thr Asp Phe Pro Gly Leu Ile Thr Leu Thr Ile Ser Leu Leu
        260                 265                 270

Asp Thr Ser Asn Leu Glu Leu Pro Glu Ala Val Val Phe Gln Asp Ser
    275                 280                 285

Val Val Phe Arg Val Ala Pro Trp Ile Met Thr Pro Asn Thr Gln Pro
290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
        435                 440                 445

Asp Phe Leu Ser Ala Gln Gln Val Gln Ala Pro Val Lys Leu Tyr Ser
    450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Asn Glu Gly His Gly Glu Ala
            500                 505                 510

Leu Leu Phe Glu Gly Ile Lys Lys Lys Gln Lys Ile Lys Asn
        515                 520                 525

Ile Leu Ser Asn Lys Thr Leu Arg Glu His Asn Ser Phe Val Glu Arg
    530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
        595                 600                 605

Arg Cys Cys Leu Glu Glu Lys Val Cys Ser Leu Leu Glu Pro Leu Gly
    610                 615                 620

Leu Gln Cys Thr Phe Ile Asn Asp Phe Phe Thr Tyr His Ile Arg His
625                 630                 635                 640

```
Gly Glu Val His Cys Gly Thr Asn Val Arg Arg Lys Pro Phe Ser Phe
                645                 650                 655
Lys Trp Trp Asn Met Val Pro
            660
```

METHODS AND KITS FOR THE DIAGNOSIS OF RHEUMATOID ARTHRITIS

RELATED APPLICATION

The present application is filed pursuant to 35 U.S.C. 371 as a U.S. National Phase application of International Patent Application No. PCT/EP09/55731, which was filed May 12, 2009, claiming the benefit of priority to European Patent Application No. EP 08 305 167.2, which was filed on May 14, 2008. The entire text of the aforementioned applications is incorporated herein by reference in its entirety.

BACKGROUND OF THE INVENTION

Rheumatoid arthritis (RA) is a chronic autoimmune disease affecting approximately 1% of the world's population. It is characterized by inflammation and cellular proliferation in the synovial lining of joints that can ultimately result in cartilage and bone destruction, joint deformity and loss of mobility. RA usually causes problems in several joints at the same time, often in a symmetric manner. Early RA tends to affect the smaller joints first, such as the joints in the wrists, hands, ankles and feet. As the disease progresses, joints of the shoulders, elbows, knees, hips, jaw and neck can also become involved. Unlike other arthritic conditions that only affect areas in or around joints, RA is a systemic disease which can cause inflammation in extra-articular tissues throughout the body including the skin, blood vessels, heart, lungs and muscles.

RA is associated with pain, deformity, decreased quality of life, and disability, which in turn affect patients' ability to lead a normal and productive life. Recent studies have shown that 5 years after the onset of the disease, approximately one third of patients with RA are no longer able to work, and within 10 years, half of the patients have substantial functional disability (A. Young et al., Rheumatology, 2007, 46: 350-357). Consequently, RA imposes an important economic burden on society. Considerable data also suggest that RA is associated with lowered life expectancy.

Although RA has been extensively studied, the etiology and pathogenesis of the disease remain incompletely understood. Factors that may increase the risk for RA include: sex of the individual (women are 2 to 3 times more likely than men to develop the disease); age (RA occurs more commonly between the ages of 40 and 60, although it can also strike children, teenagers and older adults); genetics (RA was found to be strongly associated with the inherited tissue type Major Histocompatibility Complex (MHC) antigen HLA-DR4—more specifically DRB1*0401 and DRB1*0404); and smoking (RA is about 4 times more common in smokers than non-smokers).

There is currently no reliable cure for RA. Treatment is essentially directed towards relieving pain, reducing inflammation, and stopping or slowing joint damage and bone destruction. The current therapeutic approach is to prescribe disease-modifying antirheumatic drugs (DMARDs) early in the condition, as RA patients treated early with such drugs have better outcomes, with greater preservation of function, less work disability, and smaller risk of premature death. Recent advances in the understanding of the pathophysiology of RA have led to the development of new DMARDs, called biological response modifiers. Biological DMARDs are designed to target and block the action of certain key cells or molecules, such as tumor necrosis factor-alpha (TNF-α), interleukin-1 (IL-1), T-cells, and B-cells, involved in the abnormal immune reaction associated with RA.

In comparison with traditional DMARDs, the biological agents have a much more rapid onset of action and can offer better clinical response with effective long-term prevention of joint damage (J. K. D. de Vries-Bouwstra et al., Rheum. Dis. Clin. North Am., 2005, 31: 745-762).

Since irreversible joint destruction can be prevented by intervention at the early stages of the disease, early diagnosis of RA is important. However, definitive diagnosis of RA can be difficult. Immunologic tests that can be performed for the diagnosis of RA include, in particular, measurement of the levels of rheumatoid factor (RF), antinuclear antibodies (ANA), and anti-cyclic citrunillated peptide (anti-CCP) antibodies. Serological testing for RF is complicated by moderate sensitivity and specificity, and high rates of positivity in other chronic inflammatory and infectious diseases (T. Dorner et al., Curr. Opin. Rheumatol, 2004, 16: 246-253). A positive ANA result indicates an unusually active immune system. About 40% of patients with RA are positive for ANA. However, in the first few months of the onset of the disease, ANA tests may be negative, and, in some patients, they remain negative as the disease progresses. Anti-CCP antibody testing is particularly useful in the diagnosis of RA, with high specificity, positivity early in the disease process, and ability to identify patients who are likely to have severe disease and irreversible damage. However, a negative result in anti-CCP antibody testing does not exclude RA.

Therefore, there is a great need for new biological markers of RA and RA progression. In particular, biomarkers that would allow reliable diagnosis and monitoring of the early stages of the disease and permit early intervention to potentially prevent pain, joint destruction and long-term disability, are highly desirable.

SUMMARY OF THE INVENTION

The present invention relates to improved systems and strategies for the diagnosis of rheumatoid arthritis (RA). In particular, the invention provides the identity of proteins that reflect clinically relevant disease processes in RA patients. More specifically, the invention provides biomarkers that can be used for detecting the presence of autoantibodies that are indicative of RA, in in vitro biological samples obtained from patients. In certain embodiments, the inventive biomarkers have the advantage of allowing diagnosis of RA in patients that are CCP-negative.

More specifically, in one aspect, the present invention provides an autoantigen marker comprising BRAF catalytic domain or an antibody-binding fragment thereof for use in diagnosing rheumatoid arthritis. In particular, the present invention provides an autoantigen marker comprising BRAF catalytic domain or an antibody-binding fragment thereof for use in an in vitro method of diagnosis of rheumatoid arthritis in a subject. In certain embodiments, the in vitro method of diagnosis of rheumatoid arthritis comprises steps of: contacting a biological sample obtained from the subject with the autoantigen marker for a time and under conditions allowing an antigen-antibody complex to form; and detecting any antigen-antibody complex formed, wherein the presence of an antigen-antibody complex is indicative of rheumatoid arthritis in the subject. The detection of any antigen-antibody complex formed may be performed by any suitable method, for example, by immunoassay.

In certain embodiments, the subject tested in the in vitro method of diagnostic, for example a human patient, is suspected of having rheumatoid arthritis. In certain embodiments, the subject is CCP-negative.

The biological sample used in the in vitro method of diagnostic may be selected from the group consisting of whole blood, serum, plasma, urine and synovial fluid.

In certain embodiments, the autoantigen marker comprising BRAF catalytic domain or an antibody-binding fragment thereof is immobilized on a solid carrier or support. For example, the autoantigen marker is immobilized on an array.

In certain embodiments, the BRAF catalytic domain comprised in the autoantigen marker is of human origin. For example, the BRAF catalytic domain has, comprises or is constituted by an amino acid sequence spanning from amino acid 416 to amino acid 766 of SEQ ID NO: 2.

In certain embodiments, the autoantigen marker comprising BRAF catalytic domain or an antigen-binding fragment thereof is used in an in vitro method of diagnosis of rheumatoid arthritis further comprising detecting anti-PAD4 antibodies in a biological sample obtained from the subject. In the same or other embodiments, the autoantigen marker is used in an in vitro method of diagnosis of rheumatoid arthritis further comprising measuring, in a biological sample obtained from the subject, the concentration of at least one marker selected from the group consisting of C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, and products of bone, cartilage, or synovium metabolism.

In a related aspect, the present invention provides an autoantigen marker attached to the surface of an array for use in diagnosing rheumatoid arthritis, wherein the autoantigen marker comprises BRAF catalytic domain or an antibody-binding fragment thereof. In particular, the invention provides an autoantigen marker attached to the surface of an array for use an in vitro method of diagnosis of rheumatoid arthritis in a subject, wherein the autoantigen marker comprises BRAF catalytic domain or an antibody-binding fragment thereof.

In certain embodiments, the array to which the BRAF autoantigen marker is attached further comprises, attached to its surface, an autoantigen marker comprising PAD4 or an antibody-binding fragment thereof. In the same or other embodiments, the array to which the BRAF autoantigen marker is attached further comprises, attached to its surface, at least one additional marker for detecting the presence of RA-specific autoantibodies, in particular antinuclear antibodies and anti-CCP antibodies.

In another aspect, the present invention provides the use of an autoantigen marker comprising BRAF catalytic domain or an antibody-binding fragment thereof as a marker of rheumatoid arthritis.

In still another aspect, the present invention provides a method for the in vitro diagnosis of rheumatoid arthritis in a subject, said method comprising steps of: contacting a biological sample obtained from the subject with an autoantigen marker comprising BRAF catalytic domain, or an antibody-binding fragment thereof for a time and under conditions allowing an antigen-antibody complex to form; and detecting any antigen-antibody complex formed, wherein the presence of an antigen-antibody complex is indicative of rheumatoid arthritis in the subject.

In certain embodiments, the subject, for example a human patient, is suspected of having rheumatoid arthritis. In certain embodiments, the subject, for example a human patient, is CCP-negative.

A biological sample, obtained from the subject and suitable for use in a method of diagnosis of the present invention, may be selected from the group consisting of whole blood, serum, plasma, urine, and synovial fluid.

In the methods of diagnosis provided herein, detection of any antigen-antibody complex formed between the autoantigen marker and an autoantibody present in the biological sample obtained from the subject may be performed by any suitable method. In certain embodiments, the detection is by immunoassay.

In certain embodiments, the autoantigen marker comprising BRAF catalytic domain, or an antibody-binding fragment thereof, is immobilized on a solid carrier or support.

In embodiments where the subject is a human being, BRAF catalytic domain, or an antibody-binding fragment thereof, is preferably of human origin. In certain embodiments, BRAF catalytic domain has an amino acid sequence spanning from amino acid 416 to amino acid 766 of SEQ ID NO: 2, as defined herein.

In certain embodiments, the methods of diagnosis of the present invention further comprise detecting anti-PAD4 antibodies in a biological sample obtained from the subject being tested. In these or other embodiments, the methods further comprise detecting anti-CPP antibodies in a biological sample obtained from the subject. Alternatively or additionally, the methods of diagnosis may further comprise measuring, in a biological sample obtained from the subject, the concentration of at least one marker selected from the group consisting of C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, and products of bone, cartilage, or synovium metabolism.

In yet another aspect, the present invention provides kits for diagnosis of rheumatoid arthritis in a subject. More specifically, a kit is provided for detecting anti-BRAF autoantibodies in a biological sample obtained from a subject, which comprises: an autoantigen marker comprising BRAF catalytic domain, or an antibody-binding fragment thereof; and a reagent for detection of an antigen-antibody complex formed between the autoantigen marker and an autoantibody present in the biological sample, wherein the autoantibody is an anti-BRAF autoantibody that is indicative of rheumatoid arthritis in the subject. In the kit, the autoantigen marker may be immobilized on a solid carrier or support, or, alternatively, reagents may be included in the kit that can be used to immobilize the autoantigen marker on a solid carrier or support. The kit may further comprise instructions for carrying out any of the methods of diagnosis provided herein.

In certain embodiments, the kit further comprises a second autoantigen marker comprising PAD4, or an antibody-binding fragment thereof; and a second reagent for detection of an antigen-antibody complex formed between the second autoantigen marker and an autoantibody present in the biological sample, wherein the autoantibody is an anti-PAD4 autoantibody that is indicative of RA in the subject.

In still yet another aspect, the present invention provides arrays for the diagnosis of RA in a subject. In particular, the invention provides arrays for detecting the presence of RA-specific autoantibodies in a biological sample obtained from a subject to be tested. More specifically, an array according to the invention comprises, attached to its surface, an autoantigen marker comprising BRAF catalytic domain or an antibody-binding fragment thereof, and optionally a second autoantigen marker comprising PAD4 or an antibody-binding fragment thereof. In certain embodiments, an inventive array further comprises, attached to its surface, at least one additional autoantigen marker for detecting the presence of RA-specific autoantibodies such as antinuclear antibodies and anti-CCP antibodies.

These and other objects, advantages and features of the present invention will become apparent to those of ordinary skill in the art having read the following detailed description of the preferred embodiments.

BRIEF DESCRIPTION OF THE DRAWING

FIG. 4 presents a table listing the proteins that were found to be the most often recognized by the sera of RA patients. The number of RA patients, AS patients, SLE patients, SSC patients and healthy individuals that recognized these proteins are presented in the table. Also presented are the GenBank Accession Numbers of each of the proteins' corresponding nucleotide sequences.

FIG. 5A is a graph showing the percentage of RA patients, AS patients and healthy individuals positive for PAD4, as determined by ELISA. FIG. 5B is a graph showing the percentage of RA patients expressing either two (SE+/SE+), one (SE+/SE−) or no (SE−/SE−) RA-associated HLA-DR alleles who are positive for PAD4, as determined by ELISA.

FIG. 6A is a graph showing the percentage of RA patients, AS patients and healthy individuals positive for PIP4K2C, as determined by ELISA. FIG. 6B is a graph showing the percentage of RA patients expressing either two (SE+/SE+), one (SE+/SE−) or no (SE−/SE−) RA-associated HLA-DR alleles who are positive for PIP4K2C, as determined by ELISA.

FIG. 7A is a graph showing the percentage of RA patients, AS patients and healthy individuals positive for BRAF catalytic domain, as determined by western blotting. FIG. 7B is a graph showing the percentage of RA patients expressing either two (SE+/SE+), one (SE+/SE−) or no (SE−/SE−) RA-associated HLA-DR alleles who are positive for BRAF catalytic domain, as determined by western blotting.

DEFINITIONS

Figure 1A:
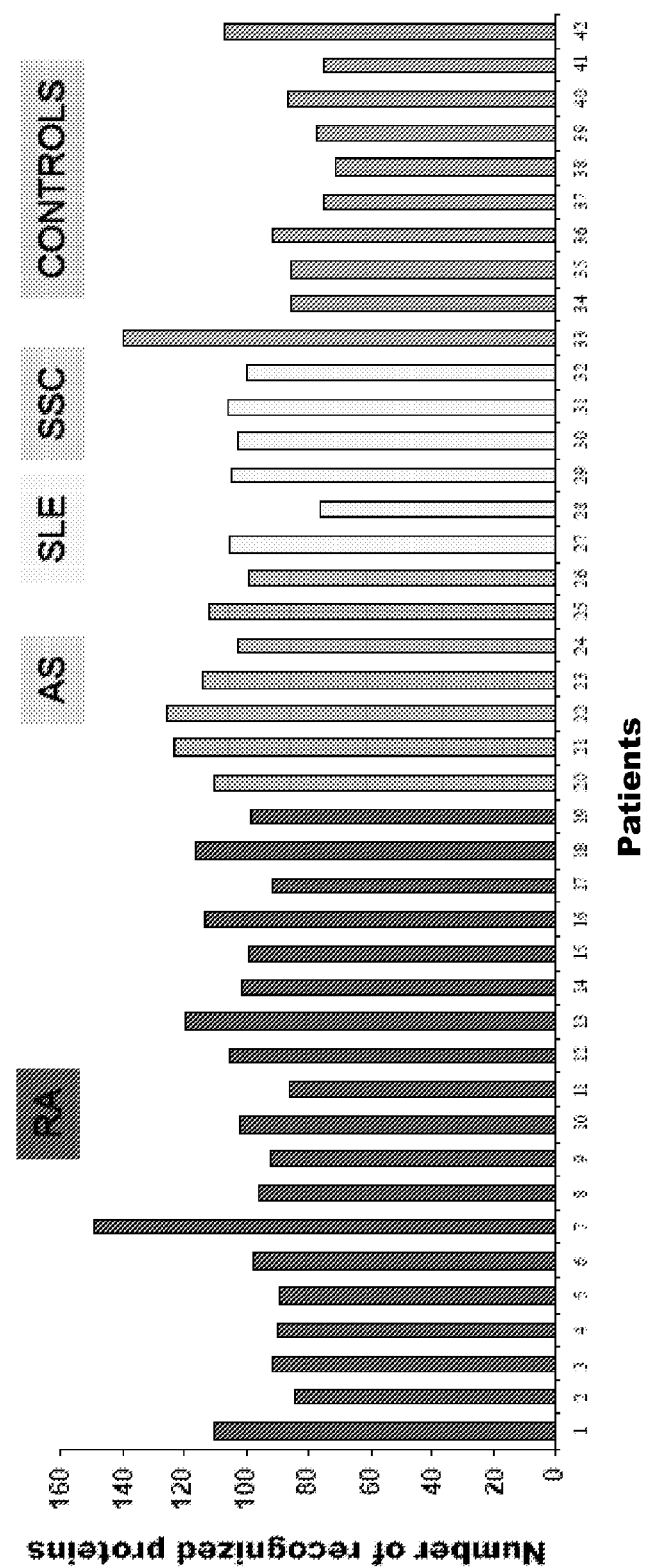
FIG. 1A is a graph showing the number of proteins of the ProtoArray Human Protein Microarray that are recognized by the serum of each of the 19 RA, 7 AS, 2 SLE, and 4 SSC patients and 10 healthy controls.

Throughout the specification, several terms are employed that are defined in the following paragraphs.

As used herein, the term "subject" refers to a human or another mammal (e.g., primate, dog, cat, goat, horse, pig, mouse, rat, rabbit, and the like), that can be afflicted with RA, but may or may not have the disease. In many embodiments of the present invention, the subject is a human being. In such embodiments, the subject is often referred to as an "individual". The term "individual" does not denote a particular age, and thus encompasses children, teenagers, and adults.

The term "subject suspected of having RA" refers to a subject that presents one or more symptoms indicative of RA (e.g., pain, stiffness or swelling of joints), or that is being screened for RA (e.g., during a physical examination). Alternatively or additionally, a subject suspected of having RA may have one or more risk factors (e.g., age, sex, family history, smoking, etc). The term encompasses subjects that have not been tested for RA as well as subjects that have received an initial diagnosis.

The term "biological sample" is used herein in its broadest sense. A biological sample is generally obtained from a subject. A sample may be of any biological tissue or fluid with which biomarkers of the present invention may be assayed. Frequently, a sample will be a "clinical sample", i.e., a sample derived from a patient. Such samples include, but are not limited to, bodily fluids which may or may not contain cells, e.g., blood (e.g., whole blood, serum or plasma), urine, synovial fluid, saliva, and joint fluid; tissue or fine needle biopsy samples, such as from bone or cartilage, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

The terms "normal" and "healthy" are used herein interchangeably. They refer to a subject that has not shown any RA symptoms, and that has not been diagnosed with RA or with cartilage or bone injury. Preferably, a normal subject is not on medication affecting RA and has not been diagnosed with any other disease (in particular an autoimmune inflammatory disease). In certain embodiments, normal subjects have similar sex, age, and/or body mass index as compared with the subject from which the biological sample to be tested was obtained. The term "normal" is also used herein to qualify a sample obtained from a healthy subject.

In the context of the present invention, the term "control", when used to characterize a subject, refers to a subject that is healthy or to a patient that has been diagnosed with a specific disease other than RA. The term "control sample" refers to one, or more than one sample, that has been obtained from a healthy subject or from a patient diagnosed with a disease other than RA.

The term "autoantibody", as used herein, has its art understood meaning, and refers to an antibody that is produced by the immune system of a subject and that is directed against one or more of the subject's own proteins. Autoantibodies may attack the body's own cells, tissues, and/or organs, causing inflammation and damage.

As used herein, the term "autoantigen" refers to an endogenous antigen, or an active fragment thereof, that stimulates the production of autoantibodies in a subject's body, as in autoimmune reactions. The term also encompasses any substances that can form an antigen-antibody complex with autoantibodies present in a subject or in a biological sample obtained from a subject.

The term "antibody-binding fragment", when used herein in connection with an antigen, refers to a fragment of the antigen that retains the ability of the antigen to bind an antibody to form an antigen-antibody complex. In particular, an antibody-binding fragment of an antigen of the present invention retains the ability to bind RA-specific autoantibodies. Suitable antibody-binding fragments of an antigen may be identified by one skilled in the art by simple trials to ascertain their ability to bind RA-specific autoantibodies.

The terms "biomarker" and "marker" are used herein interchangeably. They refer to a substance that is a distinctive indicator of a biological process, biological event, and/or pathologic condition. As used herein, the term "autoantigen marker" refers to an autoantigen, as defined herein, that is a distinctive indicator of a biological process, biological event and/or a pathologic condition involving autoantibodies.

As used herein, the term "indicative of RA", when applied to a process or event, refers to a process or event which is diagnostic of RA, such that the process or event is found significantly more often in subjects with RA than in healthy subjects and/or in subjects suffering from a disease other than RA.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the protein but need not necessarily comprise an amino acid sequence that is similar or identical to the amino acid sequence of the protein or a structure that is similar or identical to that of the protein. Preferably, in the context of the present invention, a protein analog has an amino acid sequence that is at least 30%, more preferably, at least about: 35%, 40%, 45%, 50%, 55%, 60%, 65%, 70%, 75%, 80%, 85%, 90%, 95% or 99%, identical to the amino acid sequence of the protein.

The term "protein fragment", as used herein, refers to a polypeptide comprising an amino acid sequence of at least 5 amino acid residues (preferably, at least about: 10, 15, 20, 25, 30, 40, 50, 60, 70, 80, 90, 100, 125, 150, 175, 200, or 250 amino acid residues) of the amino acid sequence of a protein. The fragment of a protein may or may not possess a functional activity of the protein.

The term "homologous" (or "homology"), as used herein, is synonymous with the term "identity" and refers to the sequence similarity between two polypeptide molecules or between two nucleic acid molecule. When a position in both compared sequences is occupied by the same base or same amino acid residue, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. Particularly preferred conservative substitutions are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

The terms "protein array" and "protein chip" are used herein interchangeably. They refer to a substrate surface on which different proteins have been immobilized, in an ordered manner, at discrete spots on the substrate. Protein arrays may be used to identify protein/protein interactions (e.g., antigen/antibody interactions), to identify the substrates of enzymes, or to identify the targets of biologically active small molecules. The term "microarray" more specifically refers to an array that is miniaturized so as to require microscopic examination for visual evaluation.

The terms "labeled", "labeled with a detectable agent" and "labeled with a detectable moiety" are used herein interchangeably. These terms are used to specify that an entity (e.g., an antigen) can be visualized, for example, following binding to another entity (e.g., an antibody). Preferably, a detectable agent or moiety is selected such that it generates a signal which can be measured and whose intensity is related to the amount of bound entity. In array-based methods, a detectable agent or moiety is also preferably selected such that it generates a localized signal, thereby allowing spatial resolution of the signal from each spot on the array. Methods for labeling proteins and polypeptides are well-known in the art. Labeled polypeptides can be prepared by incorporation of or conjugation to a label, that is directly or indirectly detectable by spectroscopic, photochemical, biochemical, immunochemical, electrical, optical, or chemical means, or any other suitable means Suitable detectable agents include, but are not limited to, various ligands, radionuclides, fluorescent dyes, chemiluminescent agents, microparticles, enzymes, colorimetric labels, magnetic labels, and haptens.

The term "treatment" is used herein to characterize a method that is aimed at (1) delaying or preventing the onset of a disease or condition; or (2) slowing down or stopping the progression, aggravating, or deteriorations of the symptoms of the condition; or (3) bringing about ameliorations or the symptoms of the condition; or (4) curing the condition. A treatment may be administered prior to the onset of the disease, for a prophylactic or preventive action. It may also be administered after initiation of the disease, for a therapeutic action.

DETAILED DESCRIPTION OF CERTAIN PREFERRED EMBODIMENTS

As mentioned above, the present invention provides autoantigen markers that can be used for detecting the presence of RA-specific autoantibodies in biological samples obtained from patients. Also provided are methods for using these autoantigen markers for the diagnosis of RA.

I—Autoantigen Markers of RA

As described in the Examples Section, the present Applicants have identified biomarkers of RA by screening sera of RA patients using the ProtoArray Human Protein Microarray commercially available from Invitrogen. This microarray contains more than 8000 human proteins, including proteases/peptidases, secreted proteins, transcription factors, cell death proteins, protein kinases, nuclear proteins, membrane proteins, and metabolism proteins. More specifically, the Applicants have screened samples of serum obtained from RA patients and from different controls, including patients suffering from spondylarthropathy (AS), systemic lupus erythematosus (SLE), and systemic sclerosis (SSC) and healthy individuals; and then compared the binding patterns for the different groups tested. They found that the majority of proteins recognized by the sera of RA patients were also recognized by the sera of controls (see FIG. 3).

The proteins that were recognized by the greater number of RA patients are listed in the table presented on FIG. 4. These proteins include: PAD4; BRAF catalytic domain; tumor suppressing subtransferable candidate 4; protein kinase C beta 1; nucleoside diphosphate linked moiety X type motif 21; nucleoside diphosphate linked moiety X type motif 21; EPH receptor B1; microtubule associated RP EB family member; PIP4K2C; protein kinase C theta; V ERB B2; calcium calmodulin dependent protein kinase II alpha; protein kinase C alpha; protein kinase C beta 1; and DEP domain 6.

Only 3 of these proteins were found to be specifically recognized by the sera of RA patients (see FIG. 4), making them potential candidate biomarkers of RA. These proteins are: PAD4 (peptidyl arginine deiminase 4), PKC beta 1 (protein kinase C beta 1) and PIP4K2C (phosphatylinositol 4 phosphate 5 kinase type II gamma). Among the RA patients tested, 47% were positive for PAD4, 31% for PKC beta 1, and 26% for PIP4K2C while individuals of the control groups were all negative for each of these proteins. In addition to these 3 candidate biomarkers, the present Applicants have singled out BRAF catalytic domain (v raf murine sarcoma viral oncogene homolog B1 catalytic domain) as this protein was found to exhibit an interesting selectivity (see FIG. 4). Indeed, in the screening experiments, 47% of the RA patients tested were found to be positive for BRAF catalytic domain versus 0% of AS patients, 0% of SLE patients, 0% of SSC patients, and 10% of healthy individuals.

As described in the Examples section, the present Applicants have then used western blotting and/or ELISA to validate the potential candidate biomarkers of RA identified in the screening experiments (i.e., PAD4, PKC beta 1, PIP4K2C and BRAF catalytic domain). This additional testing led to the validation of only 2 of the 4 candidates as autoantigen markers of RA. The validated proteins are BRAF catalytic domain and PAD4. Indeed, by screening protein array and western blotting analysis, 47% of RA patients were found to be positive for BRAF catalytic domain versus 0% of AS patients, 0% of SLE patients, 0% of SSC patients, and only 4% of healthy individuals. By screening protein array and ELISA analysis, 32% of RA patients were found to be positive for PAD4 versus 0% of AS patients, 0% of SSC patients and only 3% of healthy individuals.

Accordingly, in certain embodiments, the present invention provides an autoantigen marker comprising BRAF catalytic domain or an antibody-binding fragment or variant thereof. In other embodiments, the present invention provides an antoantigen marker comprising PAD4, or an antibody-binding fragment or variant thereof.

BRAF Catalytic Domain

BRAF (also called B-raf) is a serine-threonine kinase protein of the RAF protein family. It is involved in mitogen-activated protein kinases (MAPKs) signaling pathway, which is a conserved pathway that regulates cell growth. Signaling through this pathway is elevated in approximately 30% of human cancers. This pathway is also known to be implicated in the production of pro-inflammatory cytokines leading to joint inflammation and destruction (C. M. Crews and R. L. Erikson, Cell, 1993, 74: 215-217; T. Thalhamer et al., Rheumatology, 2008, 47: 409-414).

RAF proteins comprise an N-terminal regulatory region and a C-terminal catalytic region. They are composed of three conserved regions, CR1, CR2 and CR3. CR1 has two Ras binding domains (a Raf-like Ras binding domain: RBD, and a cysteine-rich domain: CRD); CR2 is a serine/threonine rich domain; and CR3 is the catalytic kinase domain. In humans, the BRAF gene encodes a BRAF protein of 766 amino acid residues (GenBank Accession Number: NP_004324.1), whose sequence is defined in SEQ ID NO. 1.

SEQ ID NO. 1

```
  1 MAALSGGGGG GAEPGQALFN GDMEPEAGAG AGAAASSAAD PAIPEEVWNI KQMIKLTQEH

61 IEALLDKFGG EHNPPSIYLE AYEEYTSKLD ALQQREQQLL ESLGNGTDFS VSSSASMDTV

121 TSSSSSSLSV LPSSLSVFQN PTDVARSNPK SPQKPIVRVF LPNKQRTVVP ARCGVTVRDS

181 LKKALMMRGL IPECCAVYRI QDGEKKPIGW DTDISWLTGE ELHVEVLENV PLTTHNFVRK

241 TFFTLAFCDF CRKLLFQGFR CQTCGYKFHQ RCSTEVPLMC VNYDQLDLLF VSKFFEHHPI

301 PQEEASLAET ALTSGSSPSA PASDSIGPQI LTSPSPSKSI PIPQPFRPAD EDHRNQFGQR

361 DRSSSAPNVH INTIEPVNID DLIRDQGFRG DGGSTTGLSA TPPASLPGSL TNVKALQKSP

421 GPQRERKSSS SSEDRNRMKT LGRRDSSDDW EIPDGQITVG QRIGSGSFGT VYKGKWHGDV

481 AVKMLNVTAP TPQQLQAFKN EVGVLRKTRH VNILLFMGYS TKPQLAIVTQ WCEGSSLYHH

541 LHIIETKFEM IKLIDIARQT AQGMDYLHAK SIIHRDLKSN NIFLHEDLTV KIGDFGLATV

601 KSRWSGSHQF EQLSGSILWM APEVIRMQDK NPYSFQSDVY AFGIVLYELM TGQLPYSNIN

661 NRDQIIFMVG RGYLSPDLSK VRSNCPKAMK RLMAECLKKK RDERPLFPQI LASIELLARS

721 LPKIHRSASE PSLNRAGFQT EDFSLYACAS PKTPIQAGGY GAFPVH
```

In this protein, the RBD spans from amino acids 156 to 227, the protein kinase C-conserved region 1 domain from amino acids 235 to 280, and the serine-threonine kinase catalytic domain from amino acids 456 to 712.

In the context of the present invention, the term "BRAF catalytic domain" refers to an amino acid sequence that comprises the sequence of the serine-threonine kinase catalytic domain of the BRAF protein. Thus, for example, the amino that encompasses the serine-threonine kinase catalytic domain) wherein the valine residue (V) at position 599 is replaced by a glutamate residue (E), as shown in SEQ ID NO. 2. The V599E mutation of BRAF, which is often observed in human cancers, has been demonstrated to be associated with an elevated kinase activity compared to wild-type BRAF (H. Davies et al., Nature, 2002, 417: 949-954; M. H. Andersen et al., Cancer Res., 2004, 64: 5456-5460).

SEQ ID NO. 2

```
  1 MAALSGGGGG GAEPGQALFN GDMEPEAGAG AGAAASSAAD PAIPEEVWNI KQMIKLTQEH
 61 IEALLDKFGG EHNPPSIYLE AYEEYTSKLD ALQQREQQLL ESLGNGTDFS VSSSASMDTV
121 TSSSSSSLSV LPSSLSVFQN PTDVARSNPK SPQKPIVRVF LPNKQRTVVP ARCGVTVRDS
181 LKKALMMRGL IPECCAVYRI QDGEKKPIGW DTDISWLTGE ELHVEVLENV PLTTHNFVRK
241 TFFTLAFCDF CRKLLFQGFR CQTCGYKFHQ RCSTEVPLMC VNYDQLDLLF VSKFFEHHPI
301 PQEEASLAET ALTSGSSPSA PASDSIGPQI LTSPSPSKSI PIPQPFRPAD EDHRNQFGQR
361 DRSSSAPNVH INTIEPVNID DLIRDQGFRG DGGSTTGLSA TPPASLPGSL TNVKALQKSP
421 GPQRERKSSS SSEDRNRMKT LGRRDSSDDW EIPDGQITVG QRIGSGSFGT VYKGKWHGDV
481 AVKMLNVTAP TPQQLQAFKN EVGVLRKTRH VNILLFMGYS TKPQLAIVTQ WCEGSSLYHH
541 LHIIETKFEM IKLIDIARQT AQGMDYLHAK SIIHRDLKSN NIFLHEDLTV KIGDFGLATE
601 KSRWSGSHQF EQLSGSILWM APEVIRMQDK NPYSFQSDVY AFGIVLYELM TGQLPYSNIN
661 NRDQIIFMVG RGYLSPDLSK VRSNCPKAMK RLMAECLKKK RDERPLFPQI LASIELLARS
721 LPKIHRSASE PSLNRAGFQT EDFSLYACAS PKTPIQAGGY GAFPVH
``` acid sequence of the BRAF catalytic domain may be an amino acid sequence of the BRAF protein that encompasses the sequence of the serine-threonine kinase catalytic domain of BRAF. Alternatively, the amino acid sequence of the BRAF catalytic domain may consist in the sequence of the serine-threonine kinase catalytic domain of the BRAF protein.

In the practice of the present invention, the BRAF protein may be of any suitable mammal origin (e.g., rat, dog, cattle, primate, for which the sequence of the BRAF protein has been determined or predicted). However, in embodiments where biological samples of human subjects are to be tested, the BRAF protein is preferably of human origin. The term "of human origin", as used herein to characterize a protein (or a region or fragment thereof), refers to a protein or polypeptide that is homologous to the human protein (i.e., the wild type protein naturally occurring in the human body).

Thus, in embodiments where the BRAF protein is of human origin, the term "BRAF catalytic domain" refers to an amino acid sequence that comprises the sequence spanning from amino acid 456 to amino acid 712 of SEQ ID NO. 1. Therefore, in certain embodiments, the present invention provides an autoantigen marker that comprises a sequence spanning from amino acids 456 to 712 of SEQ ID NO. 1, or an antigen-binding fragment thereof. An antigen-binding fragment of the BRAF catalytic domain is any fragment of the BRAF catalytic domain that retains the ability of the antigen to bind an RA-specific autoantibody.

On the Invitrogen human protein microarray used by the Applicants, the BRAF catalytic domain comprises an amino acid sequence spanning from amino acids 416 to 766 of SEQ ID NO. 1 (i.e., an amino acid sequence of the BRAF protein Therefore, in certain embodiments, the present invention provides an autoantigen marker that comprises a sequence spanning from amino acids 416 to 766 of SEQ ID NO. 2, or an antigen-binding fragment thereof.

The present invention also encompasses autoantigen markers comprising variants of BRAF catalytic domain or antibody-binding fragment thereof. Suitable variants include substitution variants which are conservative in nature and result from replacing one or more than one amino acid in the naturally-occurring polypeptide with another having similar structural and/or chemical properties, such as the replacement of a leucine residue with an isoleucine or valine residue, an aspartate residue with a glutamate residue, or a threonine residue with a serine residue. Other suitable variants include insertion or deletion variants, resulting from insertion or deletion of one or more than one amino acids. Suitable variants are those that retain the antigen-binding activity of the naturally-occurring polypeptide. They may be easily identified by simple antibody-binding assays.

PAD4

PAD4 (peptidyl arginine deiminase 4) is a $Ca^{2+}$-dependent enzyme that converts arginine residues into citrulline. PAD4 is widely believed to play a causative role in RA disease onset and progression because RA-associated mutations in the PAD4 gene have been identified in a variety of populations (A. Suzuki et al., Nat. Genet., 2003, 34: 395-402; T. Iwamoto et al., Rheumatology, 2006, 45: 804-807; and Y. H. Lee et al., Rheumatol. Int., 2007, 27: 827-233) and RA patients produce autoantibodies that recognize citrulline-containing proteins. It has already been shown that PAD4 is a conformation-dependent autoantigen in some RA patients (Y. Takizawa et al., Scand. J. Rheumatol., 2005, 3: 212-215).

In humans, the PAD4 protein contains 663 amino acid residues (GenBank Accession Number: NP_036519.1), and has the sequence defined in SEQ ID NO. 3.

```
                                                            SEQ ID NO. 3
  1 MAQGTLIRVT PEQPTHAVCV LGTLTQLDIC SSAPEDCTSF SINASPGVVV DIAHSPPAKK

61 KSTGSSTWPL DPGVEVTLTM KAASGSTGDQ KVQISYYGPK TPPVKALLYL TAVEISLCAD

121 ITRTGKVKPT RAVKDQRTWT WGPCGQGAIL LVNCDRDNLE SSAMDCEDDE VLDSEDLQDM

181 SLMTLSTKTP KDFFTNHTLV LHVARSEMDK VRVFQATRGK LSSKCSVVLG PKWPSHYLMV

241 PGGKHNMDFY VEALAFPDTD FPGLITLTIS LLDTSNLELP EAVVFQDSVV FRVAPWIMTP

301 NTQPPQEVYA CSIFENEDFL KSVTTLAMKA KCKLTICPEE ENMDDQWMQD EMEIGYIQAP

361 HKTLPVVFDS PRNRGLKEFP IKRVMGPDFG YVTRGPQTGG ISGLDSFGNL EVSPPVTVRG

421 KEYPLGRILF GDSCYPSNDS RQMHQALQDF LSAQQVQAPV KLYSDWLSVG HVDEFLSFVP

481 APDRKGFRLL LASPRSCYKL FQEQQNEGHG EALLFEGIKK KKQQKIKNIL SNKTLREHNS

541 FVERCIDWNR ELLKRELGLA ESDIIDIPQL FKLKEFSKAE AFFPNMVNML VLGKHLGIPK

601 PFGPVINGRC CLEEKVCSLL EPLGLQCTFI NDFFTYHIRH GEVHCGTNVR RKPFSFKWWN

661 MVP
```

As already mentioned above, the present invention provides autoantigen markers comprising PAD4 or an antibody-binding fragment thereof that can be used for the diagnosis of RA in combination with an autoantigen marker comprising BRAF catalytic domain or an antibody-binding fragment thereof. In the context of the present invention, the term "PAD4" refers to an amino acid sequence that is homologous to the naturally-occurring PAD4 protein. The PAD4 protein may be of any suitable mammal origin. However, in embodiments where biological samples from human patients are to be tested, the PAD4 protein is preferably of human origin. Thus, in certain embodiments, the present invention provides autoantigen markers comprising an amino acid sequence defined by SEQ ID NO. 3, an antibody-binding fragment thereof, or a variant thereof.

Preparation of Autoantigen Markers

The autoantigen markers of the present invention may be prepared by any suitable method, including chemical synthesis and recombinant methods.

The biomarkers of the invention are generally sufficiently short that chemical synthesis, using standard methods is feasible. Solid-phase peptide synthesis, which was initially described by R. B. Merrifield (J. Am. Chem. Soc. 1963, 85: 2149-2154) is a quick and easy approach to synthesizing peptides and small peptidic molecules of known sequences. A compilation of such solid-phase techniques may be found, for example, in "Solid Phase Peptide Synthesis" (Methods in Enzymology, G. B. Fields (Ed.), 1997, Academic Press: San Diego, Calif., which is incorporated herein by reference in its entirety). Most of these synthetic procedures involve the sequential addition of one or more amino acid residues or suitably protected amino acid residues to a growing peptide chain. For example, the carboxy group of the first amino acid is attached to a solid support via a labile bond, and reacted with the second amino acid, whose amino group has, beforehand, been chemically protected to avoid self-condensation. After coupling, the amino group is deprotected, and the process is repeated with the following amino acid. Once the desired peptide is assembled, it is cleaved off from the solid support, precipitated, and the resulting free peptide may be analyzed and/or purified as desired. Solution methods, as described, for example, in "The Proteins" (Vol. II, 3$^{rd}$ Ed., H. Neurath et al. (Eds.), 1976, Academic Press: New York, N.Y., pp. 105-237) may also be used to synthesize the biomarkers of the invention.

Alternatively, the autoantigen markers provided herein can be produced by recombinant DNA methods. These methods generally involve isolation of the gene encoding the desired protein, transfer of the gene into a suitable vector, and bulk expression in a cell culture system. The DNA coding sequences for the polypeptides of the invention are sufficiently short to be readily prepared synthetically using methods known in the art (see, for example, M. P. Edge et al., Nature, 1981, 292: 756-762).

After synthesis, the DNA encoding the desired peptide is inserted into a recombinant expression vector, which may be a plasmid, phage, viral particle, or other nucleic acid molecule containing vectors or nucleic acid molecule containing vehicles which, when introduced into an appropriate host cell, contains the necessary genetic elements to direct expression of the coding sequence of interest. Standard techniques well known in the art can be used to insert the nucleic acid molecule into the expression vector. The insertion results in the coding sequence being operatively linked to the necessary regulatory sequences.

Host cells for use in the production of proteins are well known and readily available. Examples of host cells include bacteria cells such as *Escherichia coli, Bacillus subtilis*, attenuated strains of *Salmonella typhimurium*, and the like; yeast cells such as *Saccharomyces cerevisiae, Schizosaccharomyces pombe, Kluyveromyces* strains, *Candida*, or any yeast strain capable of expressing heterologous proteins; insect cells such as *Spodoptera frugiperda*; non-human mammalian tissue culture cells such as Chinese Hamster Ovary (CHO) cells, monkey COS cells, and mouse 3T3 cells; and human tissue culture cells such as HeLa cells, HL-60 cells, kidney 293 cells and epidermal S431 cells.

Several expression vectors to produce polypeptides in well known expression systems are commercially available. For example, the plasmids pSE420 (available from Invitrogen, San Diego, Calif.) and pBR322 (available from New England Biolabs, Beverly, Mass.) may be used for the production of the inventive peptides in *E. coli*. Similarly, the plasmid pYES2 (Invitrogen) may be used for peptide production in *S. cerevisiae* strains of yeast. The commercially available Mac-BacR™ kit (Invitrogen) for baculovirus expression system or the BaculoGold™ Transfection Kit available from PharMingen (San Diego, Calif.) may be used for production in insect cells, while the plasmids pcDNA I, pcDNA 3, and pRc/RSV, commercially available from Invitrogen, may be used for the production of the peptides of the invention in mammalian cells such as Chinese Hamster Ovary (CHO) cells.

Other expression vectors and systems can be obtained or produced using methods well known to those skilled in the art. Expression systems containing the requisite control sequences, such as promoters and polyadenylation signals, and preferably enhancers are readily available for a variety of hosts (see, for example, Sambrook et al., *Molecular Cloning: A Laboratory Manual*, 2$^{nd}$ Ed., 1989, Cold Spring Harbor Press: Cold Spring, N.Y.; and R. Kaufman, Methods in Enzymology, 1990, 185: 537-566).

The expression vector including the DNA that encodes the desired protein is used to transform the compatible host cell. The host cell is then cultured and maintained under conditions favoring expression of the desired protein. The protein thus produced is recovered and isolated, either directly from the culture medium or by lysis of the cells. It can then be characterized by different methods such as Nuclear Magnetic resonance (NMR) and X-ray crystallography.

As understood by one skilled in the art, an autoantigen marker of the present invention may be produced as a fusion protein (i.e., a molecule where the antibody-binding moiety, e.g., BRAF catalytic domain, is linked to a polypeptide entity). Such a polypeptide entity may be selected to confer any of a number of advantageous properties to the resulting fusion protein. For example, the polypeptide entity may be selected to provide increased expression of the recombinant fusion protein. Alternatively or additionally, the polypeptide entity may facilitate purification of the fusion protein by, for example, acting as a ligand in affinity purification. A proteolytic cleavage site may be added to the recombinant protein so that the desired sequence can ultimately be separated from the polypeptide entity after purification. The polypeptide entity may also be selected to confer an improved stability to the fusion protein, when stability is a goal. Examples of suitable polypeptide entities include, for example, polyhistidine tags, that allow for the easy purification of the resulting fusion protein on a nickel chelating column. Glutathione-S-transferase (GST), maltose B binding protein, or protein A are other examples of suitable polypeptide entities that can be fused to BRAF catalytic domain (or PAD4) using commercial fusion expression vectors.

Alternatively, autoantigen markers of the invention may be prepared using commercially available BRAF catalytic domain (e.g., from Invitrogen) or PAD4.

In certain embodiments, an autoantigen marker of the invention is provided immobilized onto a solid carrier or support (e.g., a bead or array). Methods for immobilizing polypeptide molecules onto a solid surface are known in the art. In particular, the invention provides an array for the diagnosis of RA, comprising, immobilized to its surface, an autoantigen marker comprising BRAF catalytic domain, or an antibody-binding fragment thereof, and, at least one other biomarker of RA. In certain embodiments, the at least one other biomarker of RA is an autoantigen marker comprising PAD4, or an antibody-binding fragment thereof. Alternatively or additionally, the array may further comprise, immobilized to its surface, biomarkers allowing detection of the presence of antinuclear antibodies and/or anti-CCP antibodies in a biological sample obtained from a subject. The terms "array for the diagnosis of RA" and "array for diagnosing RA" are used herein interchangeably. They refer more specifically to an array for the detection of RA-specific autoantibodies in a biological sample.

II—Diagnosis Methods

An inventive autoantigen marker may be used to detect, in a biological sample obtained from a subject, the presence of autoantibodies that are indicative of RA.

Accordingly, the present invention provides methods for diagnosing RA in a subject. Such methods comprise contacting a biological sample obtained from the subject with an inventive autoantigen marker for a time and under conditions allowing an antigen-antibody complex to form between the autoantigen marker and an autoantibody present in the biological sample; and detecting the presence or absence of any antigen-antibody complex formed, wherein the presence of an antigen-antibody complex is indicative of RA in the subject.

In particular, the present invention provides methods for diagnosing RA in a subject by detecting the presence of anti-BRAF autoantibodies in a biological sample using an autoantigen marker comprising BRAF catalytic domain or an antibody-binding fragment thereof. Such methods may further comprise detecting the presence of anti-PAD4 autoantibodies in the biological sample using an autoantigen marker comprising PAD4 or an antibody-binding fragment thereof.

Biological Samples

The methods of diagnosis of the present invention may be applied to the study of any type of biological samples allowing one or more inventive biomarkers to be assayed. Examples of suitable biological samples include, but are not limited to, urine, whole blood, serum, plasma, saliva, and synovial fluid. Biological samples used in the practice of the invention may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy.

In preferred embodiments, the inventive methods are performed on the biological sample itself without, or with limited, processing of the sample.

However, alternatively, the inventive methods may be performed on a protein extract prepared from the biological sample. In this case, the protein extract preferably contains the total protein content. Methods of protein extraction are well known in the art (see, for example "*Protein Methods*", D. M. Bollag et al., 2$^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, 2$^{nd}$ Ed., 2001, Oxford University Press; "*Principles and Reactions of Protein Extraction, Purification, and Characterization*", H. Ahmed, 2005, CRC Press: Boca Raton, Fla.). Various kits can be used to extract proteins from bodily fluids and tissues. Such kits are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation.

Detection of Antigen-Antibody Complexes

The diagnostic methods of the present invention generally involve detection of a complex formed between the autoantigen marker and an RA-specific autoantibody present in a biological sample. In the practice of the invention, detection of such an antigen-antibody complex may be performed by any suitable method (see, for example, E. Harlow and A. Lane, "*Antibodies: A Laboratories Manual*", 1988, Cold Spring Harbor Laboratory: Cold Spring Harbor, N.Y.).

For example, detection of an antigen-antibody complex may be performed using an immunoassay. A wide range of immunoassay techniques is available, including radioimmunoassay, enzyme immunoassays (EIA), enzyme-linked immunosorbent as says (ELISA), and immunofluorescence immunoprecipitation. Immunoassays are well known in the art. Methods for carrying out such assays as well as practical applications and procedures are summarized in textbooks. Examples of such textbooks include P. Tijssen, In: Practice and theory of enzyme immunoassays, eds. R. H. Burdon and v. P. H. Knippenberg, Elsevier, Amsterdam (1990), pp. 221-278 and various volumes of Methods in Enzymology, Eds. S. P. Colowick et al., Academic Press, dealing with immunological detection methods, especially volumes 70, 73, 74, 84, 92 and 121. Immunoassays may be competitive or non-competitive.

For example, any of a number of variations of the sandwich assay technique may be used to perform an immunoassay. Briefly, in a typical sandwich assay applied to the detection of RA-specific autoantibodies according to the present invention, an unlabeled autoantigen marker is immobilized on a solid substrate and the sample to be tested is brought into contact with the bound autoantigen marker for a time and under conditions allowing formation of an antigen-antibody complex. Following incubation, an antibody that is labeled with a detectable moiety and that specifically recognizes antibodies from the species tested (e.g., an anti-human IgG for human subjects) is added and incubated under conditions allowing the formation of a ternary complex between any autoantigen-bound autoantibody and the labeled antibody. Any unbound material is washed away, and the presence of any RA-specific autoantibody in the sample is determined by observation of the signal directly or indirectly produced by the detectable moiety. Variations on this assay include an assay, in which both the biological sample and the labeled antibody are added simultaneously to the immobilized autoantigen marker.

An autoantigen marker may be immobilized by being either covalently or passively bound to the surface of a solid carrier or support. Examples of suitable carrier or support materials include, but are not limited to, agarose, cellulose, nitrocellulose, dextran, Sephadex, Sepharose, carboxymethyl cellulose, polyacrylamides, polystyrene, polyvinyl chloride, polypropylene, gabbros, filter paper, magnetite, ion-exchange resin, glass, polyamine-methyl vinyl-ether-maleic acid copolymer, amino acid copolymer, ethylene-maleic acid copolymer, nylon, silk, and the like. Immobilization of an autoantigen marker on the surface of a solid carrier or support may involve crosslinking, covalent binding or physical adsorption, using methods well known in the art. The solid carrier or support may be in the form of a bead, a particle, a microplate well, an array, a cuvette, a tube, a membrane or any other shape suitable for conducting an immunoassay. In certain embodiments, immobilization of an autoantigen marker to a solid carrier or support includes gel electrophoresis followed by transfer to a membrane (typically nitrocellulose or PVDF) in a process called western blotting (or immunoblot) well known in the art.

The second antibody (i.e., the antibody added in a sandwich assay as described above) may be labeled with any suitable detectable moiety, i.e., any entity which, by its chemical nature, provides an analytically identifiable signal allowing detection of the ternary complex, and consequently detection of the autoantigen-autoantibody complex.

Detection may be either qualitative or quantitative. Methods for labeling biological molecules such as antibodies are well-known in the art (see, for example, "*Affinity Techniques. Enzyme Purification: Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

The most commonly used detectable moieties in immunoassays are enzymes and fluorophores. In the case of an enzyme immunoassay (EIA), an enzyme such as horseradish perodixase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable colon change, upon hydrolysis of the corresponding enzyme. In the case of immunofluorescence, the second antibody is chemically coupled to a fluorescent moiety without alteration of its binding capacity. After binding of the fluorescently labeled antibody to the antigen-antibody complex and removal of any unbound material, the fluorescent signal generated by the fluorescent moiety is detected, and optionally quantified. Alternatively, the second antibody may be labeled with a radioisotope, a chemiluminescent moiety, or a bioluminescent moiety.

RA Diagnosis

In the methods of the present invention, detection of an antigen-antibody complex is indicative of the presence of RA-specific autoantibodies in the biological sample tested and is therefore indicative of RA in the subject from which the biological sample has been obtained. Thus, methods of the present invention may be used for diagnosis of RA in patients. In particular, methods of the invention may be used for testing subjects suspected of having RA. In addition, methods of the present invention using an autoantigen marker comprising BRAF catalytic domain or an antibody-binding fragment thereof may be used to diagnose RA in CCP-negative patients. Indeed, the present Applicants have shown that 33% of RA patients positive for BRAF catalytic domain were CCP-negative.

It will be appreciated by one skilled in the art that diagnosis of RA may be made solely on the results provided by a method provided herein. Alternatively, a physician may also consider other clinical or pathological parameters used in existing methods to diagnose RA. Thus, results obtained using methods of the present invention may be compared to and/or combined with results from other tests, assays or procedures performed for the diagnosis of RA. Such comparison and/or combination may help provide a more refine diagnosis.

For example, RA diagnosis methods of the present invention may be used in combination with ARA criteria (i.e., the American College of Rheumatology 1987 revised criteria for the classification of RA described in F. C. Arnett et al., Arthritis Rheum., 1988, 31: 315-324). According to the ARA criteria, a patient is said to have RA if the patient exhibits at least 4 of the 7 following criteria: 1) morning stiffness for at least 1 hour; 2) arthritis of 3 or more joint areas; 3) arthritis of hand joints; 4) symmetrical arthritis; 5) rheumatoid nodules; 6) serum rheumatoid factor (RF); and 7) radiographic changes, wherein criteria 1-4 must be present for at least 6 months.

Alternatively or additionally, results from RA diagnosis methods of the present invention may be used in combination with results from one or more assays that employ other RA biomarkers. Thus, in certain embodiments, diagnostics of RA may be based on results from a method of the invention and on results from one or more additional assays using a different RA biomarker. For example, a panel of RA biomarkers may be tested either individually or simultaneously, e.g., using a chip or a bead-based array technology.

Examples of suitable RA biomarkers include, but are not limited to, CCP, C-reactive protein, serum amyloid A, interleukin 6 (IL6), S100 proteins, ostopontin, rheumatoid factor, matrix metalloprotease 1 (MMP-1), matrix metalloprotease 3 (MMP-3), hyaluronic acid, sCD14, angiogenesis markers (such as the vascular endothelial growth factor or VEGF), and products of bone, cartilage or synovium metabolism (such as pyridinoline or its glycosylated form; deoxy-pyridinoline; cross-linked telopeptides; collagen neoepitopes; CS846; cartilage oligomeric matrix protein; cartilage intermediate layer protein; matrilins, chondromodulatins, osteocalcin, and the like).

III—Kits

In another aspect, the present invention provides kits comprising materials useful for carrying out diagnostic methods according to the present invention. The diagnosis procedures provided herein may be performed by diagnostics laboratories, experimental laboratories, or practitioners. The invention provides kits that can be used in these different settings.

Materials and reagents for detecting RA-specific autoantibodies in a biological sample and/or for diagnosing RA in a subject according to the present invention may be assembled together in a kit. Each kit of the invention comprises at least one inventive autoantigen marker, preferably in an amount that is suitable for detection of autoantibodies in a biological sample. Thus, in certain embodiments, an inventive kit comprises an autoantigen marker comprising BRAF catalytic domain or an antigen-binding fragment thereof. In other embodiments, an inventive kit comprises a first autoantigen comprising BRAF catalytic domain or an antigen-binding fragment thereof, and a second autoantigen comprising PAD4 or an antigen-binding fragment thereof. The autoantigen marker(s) may or may not be immobilized on a substrate surface (e.g., beads, array, and the like). For example, an inventive kit may include an array for diagnosing RA as provided herein. Alternatively, a substrate surface (e.g., membrane) may be included in an inventive kit for immobilization of the autoantigen marker (e.g., via gel electrophoresis and transfer to a membrane).

In addition, an inventive kit generally also comprises at least one reagent for the detection of an antigen-antibody complex formed between the autoantigen marker included in the kit and an autoantibody present in a biological sample. Such a reagent may be, for example, a labeled antibody that specifically recognizes antibodies from the species tested (e.g., an anti-human IgG for human subjects), as described above.

Depending on the procedure, the kit may further comprise one or more of: extraction buffer and/or reagents, western blotting buffer and/or reagents, immunodetection buffer and/or reagents, labeling buffer and/or reagents, and detection means. Protocols for using these buffers and reagents for performing different steps of the procedure may be included in the kit.

The different reagents included in an inventive kit may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the diagnosis of RA in a subject according to a method of the invention. Instructions for using the kit according to methods of the invention may comprise instructions for processing the biological sample obtained from the subject and/or for performing the test, or instructions for interpreting the results. A kit may also contain a notice in the form prescribed by a governmental agency regulating the manufacture, use or sale of pharmaceuticals or biological products.

IV—Development of New Therapeutics for RA

The BRAF catalytic domain may be an attractive target for the identification of compounds or substances potentially useful for treating RA or preventing RA progression. For example, screens may be developed to identify compounds or substances that have a neutralizing or inhibiting activity against BRAF catalytic domain.

Such screens may be carried out in any suitable biological system such as a biological fluid, a biological fluid, or cells. Generally, screens are performed using cells that can be grown in standard tissue culture ware. Suitable cells include all appropriate normal and transformed cells derived from any recognized sources. Preferably, cells are of mammalian (human or animal, such as rodent or simian) origin. More preferably, cells are of human origin. Mammalian cells may be of any organ or tissue origin (e.g., bone, cartilage, or synovial fluid) and of any cell types as long as the cells express BRAF. Cells to be used in the practice of the methods of the present invention may be primary cells, secondary cells, or immortalized cells (e.g., established cell lines). They may be prepared by techniques well known in the art (for example, cells may be isolated from bone, cartilage or synovial fluid) or purchased from immunological and microbiological commercial resources (for example, from the American Type Culture Collection, Manassas, Va.). Alternatively or additionally, cells may be genetically engineered to contain, for example, a gene of interest. An assay developed for primary drug screening (i.e., first round(s) of screening) is preferably performed using established cell lines, which are commercially available and usually relatively easy to grow, while an assay to be used later in the drug development process is preferably performed using primary and secondary cells, which are generally more difficult to obtain, maintain and/or grow than immortalized cells but which represent better experimental models for in vivo situation. Screening methods may be performed using cells contained in a plurality of wells of a multi-well assay plate.

As will be appreciated by one of ordinary skill in the art, any kind of compounds or agents can be screened. A candidate compound may be a synthetic or natural compound; it may be a single molecule or a mixture or complex of different molecules. Candidate compounds may be screened individually. Alternatively, compounds comprised in collections or libraries may be screened simultaneously.

Collections of natural compounds in the form of bacterial, fungal, plant and animal extracts are available from, for example, Pan Laboratories (Bothell, Wash.) or MycoSearch (Durham, N.C.). Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means. Chemical libraries are relatively easy to prepare by traditional automated synthesis, PCR, cloning or proprietary synthetic methods (see, for example, S. H. DeWitt et al., Proc. Natl. Acad. Sci. U.S.A. 1993, 90:6909-6913; R. N. Zuckermann et al., J. Med. Chem. 1994, 37: 2678-2685; Carell et al., Angew. Chem. Int. Ed. Engl. 1994, 33: 2059-2060; P. L. Myers, Curr. Opin. Biotechnol. 1997, 8: 701-707).

Using the BRAF catalytic domain as a target, useful agents for the treatment of RA may be found in any of a large variety of classes of chemicals.

It is also envisioned to develop anti-BRAF catalytic domain antibodies as therapeutic tools for the treatment of RA. Anti-TNF alpha antibodies and anti-CD20 antibodies are currently used in the treatment of RA. In patients treated with anti-CD20 antibodies, a high clinical response is observed, which results from depletion of B cells and, consequently from depletion of all B-cell antibodies. However, indiscriminate depletion of all types of B cell antibodies may potentially cause a weakening of the immune system. Anti-BRAF catalytic domain antibodies, which offer the advantage of a more targeted action, may overcome the limitations and potential problems associated with injection of anti-CD20 antibodies.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Most of the results presented below have been reported by the present Applicants in a scientific article (I. Auger et al., "New Autoantigens in Rheumatoid Arthritis: Screening 8268 Protein Arrays with RA Patient's Sera", Annals Rheumatic Disease, 2009, 68(4): 591-594), which is incorporated herein by reference in its entirety.
Introduction Two elements are important to the development of RA: HLA-DR genes and autoantibodies. RA is under the control of HLA-DR genes, which display allelic polymorphism. HLA-DR alleles can be susceptible (for example, HLA-DRB1*0401, *0404, *0101, *0102, *1001), neutral (for example, HLA-DR15) or protective (for example, HLA-DRB1*07, *08, *0402) towards the development of RA (P. K. Gregersen et al., Arthritis and Rheumatism, 1987, 30: 1205-1213; D. Reviron et al., Arthritis and Rheumatism, 2001, 44: 535-540). The risk of developing RA is controlled by the two HLA-DR alleles that an individual expresses, and can be assessed by genotyping the individual for HLA-DR (W. Thomson et al., Arthritis Rheum., 1999, 42: 757-762).

The present Applicants have HLA-DR-genotyped every RA patient in the Rheumatology ward at the La Conception Hospital in Marseille, France, since 1992. By comparing 1000 RA patients with 500 controls, they have obtained an HLA-DR genotypic risk table indicating the relative risk of developing RA for each of the 72 most common genotypes in the population. The extraordinary synergy between HLA-DRB1*0401 and HLA-DRB1*0404, and the very strong protection conferred by HLA-DRB1*07 were confirmed. These experiments also unexpectedly demonstrated that the DR7/DR9 genotype confers a very high risk of developing RA despite not containing any susceptible allele.

RA is an antoantibody-mediated disease. The most critical autoantibodies in RA are directed at citrullin residues on proteins such as Fibrin, Filaggrin, and Vimentin. The present Applicants have recently observed that HLA-DRB1*0404 is also associated with anti-citrullinated fibrinogen in the sera of RA patients. Indeed, 83% of RA patients expressing HLA-DRB1*0404 were found to have antibodies to citrullinated fibrinogen (I. Auger et al., Arthritis and Rheumatism, 2005, 52: 3424-3432). However, non-citrullinated proteins, such as calpastatin, are also targeted by autoantibodies from RA patients. By screening synovial proteins with sera of RA patients homozygous for HLA-DR alleles, the present Applicants observed that sera of RA patients homozygous for HLA-DRB1*0404 recognized a 100 kD synovial protein identified as calpastatin, the natural inhibitor of calpains (proteases involved in cartilage destruction). Indeed, 50% of RA patients expressing HLA-DRB1*0404 have antoantibodies to synovial calpastatin (I. Auger et al., Annals of Rheumatic Diseases, 2007, 66: 1588-1593). The data obtained by the Applicants support the idea that HLA-DRB1*0404 carries an original function allowing its association with many autoantibody responses in RA.

In the study presented below, the present Applicants have used sera from RA patients with particular HLA-DR genotypes: HLA-DRB1*0401/0404, *0401/0401, *0404/0404, *0404/07, *0401/07, *07/07, *09/07, to screen protein arrays containing more than 8000 human proteins, in order to identify specific autoantibody patterns
Patients and Methods
Sera of RA Patients for Protein Microarray Analysis Nineteen (19) RA patients from the Rheumatology unit at the La Conception Hospital in Marseille, France, were selected for this study. All RA patients fulfilled the American College of Rheumatology 1987 revised criteria (F. C. Arnett et al., Arthritis Rheum., 1988, 31: 315-324). HLA-DR oligotyping was performed for each patient (O. Ollerup et al., Tissue Antigens, 1992, 39: 225-235). Three of the patients were found to express both HLA-DRB1*0401 and HLA-DRB1*0404, 4 patients were homozygous for HLA-DRB1*0401, 3 patients were homozygous for HLA-DRB1*0404, 2 patients expressed both HLA-DRB1*0401 and HLA-DR7, 2 patients expressed both HLA-DRB1*0404 and HLA-DR7, 1 patient expressed HLA-DR7 and HLA-DR13, 2 patients were homozygous for HLA-DR7, and 2 patients expressed the unexpected high risk genotype HLA-DR7/DR9.
Sera of Controls for Protein Microarray Analysis The control groups were composed of: 7 patients with spondylarthropathy (AS) and 2 patients with systemic lupus erythematosus (SLE) from the Rheumatology unit at La Conception Hospital in Marseille; 4 patients with systemic sclerosis (SSC) from a national cohort elaborated in collaboration with Hospital Cochin, Hospital Saint Antoine, and Hospital Saint Louis in Paris, France, Hospital Claude Huriez in Lille, France, and Hospital La Conception, in Marseille. Ten healthy controls were recruited among laboratory staff volunteers and volunteer bone marrow donors after health evaluation to discard autoimmune pathologies. All participants gave informed consent.
Human Protein Microarray The "ProtoArray Human Protein Microarray", commercially available from Invitrogen, was used in the present study. This microarray contains 8268 human proteins (G. A. Michaud et al., "Biomarker identification using Protoarray high density protein microarrays: Profiling autoantibodies in disease", Invitrogen Note Information; M. E. Hudson et al., Proc. Natl. Acad. Sci. USA, 2007, 44: 17494-17499).

Two percent (2%) of the proteins on the ProtoArray Human Protein Microarray are proteases/peptidases, 2% secreted proteins, 3% transcription factors, 3% cell death proteins, 5% protein kinases, 11% nuclear proteins, 17% membrane proteins, and 31% metabolism proteins (data from Protein Content list 4.0 provided by Invitrogen). All the proteins on the microarray were expressed as GST fusion proteins (as described below), purified under native conditions, and spotted in duplicate on nitrocellulose-coated glass slides. This human protein collection is derived from the human Ultimate ORF Clone Collection (data from http://orf.invitrogen.com). Each clone was sequence-checked on GenBank. Each of the clones used to generate the human protein collection was a human ORF cloned into a Gateway® vector. Each expression clone was used to express a protein of interest as an N-terminal GST-fusion protein using a baculovirus expression system. The molecular weight of each expressed protein was determined by western blotting.

Serum Profiling Assays on Protein Arrays

Array slides were blocked with 1% BSA/PBST, and then incubated in the presence of serum samples (in phosphate buffered saline with Tween 20) for 1 hour at 4° C. Array slides were then probed with diluted (1:500) human serum for 1.5 hour at 4° C. After washing with PBST, 1 μg/mL of anti-human IgG conjugated to Alexa Fluor® 647 dye was added to the slides. The slides were then washed and dried (Partnership, Evry, France). A negative control experiment was performed, in parallel, on a separate slide. In the control, the slide was treated under the same conditions as described above except that it was incubated with buffer in the absence of serum. The purpose of this control is to provide reference points for data acquisition and analysis.

Data Acquisition/Analysis

Array slides were scanned using a GenePix® 4000B Fluorescent Scanner. Data were acquired with GenePix® Pro software and processed using ProtoArray™ Prospector 2.0.

Data Analysis

In order to identify autoantigens among the proteins of the microarray, a panel of values was calculated for each array protein, including the Z-score, the CI P-value (Chebyshev's Inequality Precision Value) and the CV. The Z-Score was calculated based on the signal from the protein spots on the array compared to all protein features. The Z-score is the signal used value minus the mean signal used value from all the human protein features on the array, divided by the standard deviation on the signal used values for all the human protein features. The CI P-value evaluates the strength relative to all negative control spots and calculates the probability that the observed signal comes from the negative control distribution. The lower the CI P-value, the greater the probability that the signal is not due to a random event. The CV evaluates the similarity between duplicates. A protein was identified as an immunoreactive autoantigen if: Z-score>3.0, CIP P-value<0.05 and CV<0.5.

RA Patients and Controls for ELISA and Western Blot Analysis

For these experiments, patients with RA and patients with spondylarthropathy (AS) from the Rheumatology Ward at the La Conception Hospital in Marseille were selected. All the RA patients fulfilled the 1987 American College of Rheumatology criteria for RA. Volunteers from the laboratory staff and the Marseille Blood Transfusion Center staff served as normal controls. HLA-DR oligotyping was performed for each of the patients and normal controls. Informed consent was obtained from all participants.

Detection of Autoantibodies by ELISA

Plates were coated overnight with 0.1 μg/mL of a protein of interest (i.e., a candidate autoantigen marker identified in the microarray experiments) diluted in phosphate buffer saline (PBS), pH 7.4. Plates were blocked with PBS containing 5% milk, and then incubated for 3 hours in the presence of sera diluted to 1:100 in PBS. After washing with 0.1% Tween 20, peroxidase conjugated anti-human IgG (Sigma, France) was added to the plates. Optical density (OD) was read at 405 nm. Background OD was obtained by measuring the optical density of each serum added to a well of the plate that did not contain the protein of interest. A serum was considered as positive for the protein if the OD value measured was more than twice the background OD.

Detection of Autoantibodies by Western Blotting

Proteins (i.e., candidate autoantigen markers identified in the microarray experiments) were separated on 10% SDS PAGE gels and transferred onto PVDF membranes. Blots were incubated in the presence of sera of patients or controls followed by peroxidase-conjugated anti-human IgG. Detection was carried out by chemiluminescence (Roche Diagnostics, Meylan, France).

Results

Autoantibodies Pattern Associated with RA Patients

Sera from 19 RA patients, and 23 controls (7 from spondylarthropathy patients (AS); 2 from lupus patients (SLE); 4 from systemic sclerosis patients (SSC); and 10 from healthy individuals) were used to probe arrays containing 8268 human proteins. The presence of autoantibodies bound to proteins on the array was detected by a fluorescently labeled anti-human IgG antibody. Immunoreactive autoantigens were defined by a Z-score>3.0, a CI P-value<0.05 and a CV<0.5.

Figure 1B:
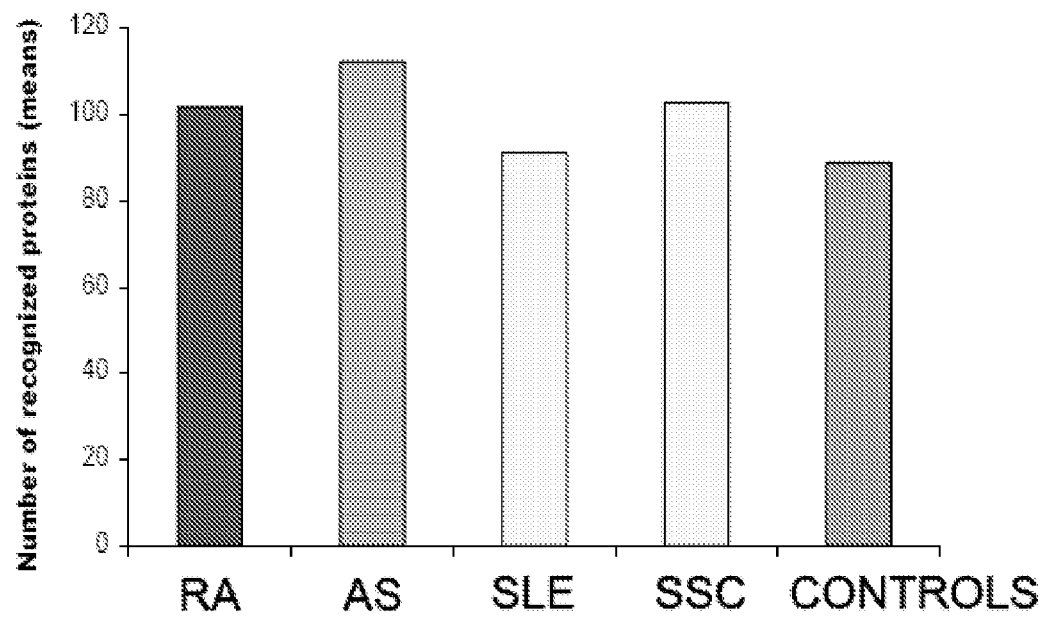
FIG. 1B is a graph showing the mean number of proteins of the Protein Microarray that are recognized by each group of patients and healthy controls.

FIG. 1A presents the number of proteins that are recognized by each patient and control tested in this study. The number of proteins recognized by each group of participants was found to be very similar, as shown in FIG. 1B and the table below.

| Mean number of proteins recognized by each group of patients and healthy controls. | | | | |
|---|---|---|---|---|
| | RA | AS | SLE | SSE | Healthy controls |
| Number of proteins recognized (mean value) | 101 | 112 | 91 | 103 | 89 |

Among the 19 RA patients (who were numbered 1 to 19), 14 were CCP-positive (patients 2-5, 7-9, 11, 12, 14-17, and 19) and 5 were CCP-negative (patients 1, 6, 10, 13, and 18). The number of proteins recognized by the group of CCP-positive RA patients was comparable to the number of proteins recognized by the group of CCP-negative RA patients (see table below).

| Mean number of proteins recognized by the CCP-positive and CCP-negative RA patients | | |
|---|---|---|
| | CCP-positive | CCP-negative |
| Number of proteins recognized (mean value) | 99 | 109 |

Among the RA patients tested, 10 had been suffering from RA for less than 10 years (patients 6 and 8-16) and 9 had been suffering from RA for more than 10 years (patients 1-5, 7, and 17-19). The number of proteins recognized by RA patients was found to be independent of disease duration (see table below).

| Mean number of proteins recognized by patients with RA for less or more than 10 years | | |
| --- | --- | --- |
|  | less than 10 years | more than 10 years |
| Number of proteins recognized (mean value) | 101 | 102 |

In summary, the mean number of proteins recognized by RA patients did not significantly differ from the number of proteins recognized by the different controls. Disease duration and CCP-reactivity were also found not to affect the number of proteins recognized by RA patients.

Autoantibodies Pattern Associated with HLA-DR Genotype in RA Patients

The sera from RA patients with HLA-DR genotypes associated with high or low risk to develop the disease were tested to compare their reactivity pattern on protein arrays. As already mentioned above, HLA-DR genotypes containing two susceptibility alleles confer a higher risk than genotypes containing only one susceptibility allele, which itself confers a higher risk than DR genotypes containing no susceptibility allele. Three (3) patients expressing both HLA-DRB1*0401 and HLA-DRB1*0404, 4 patients homozygous for HLA-DRB1*0401, 3 patients homozygous for HLA-DRB1*0404, 2 patients expressing both HLA-DRB1*0401 and HLA-DR7, 2 patients expressing both HLA-DRB1*0404 and HLA-DR7, 1 patient expressing HLA-DR7 and HLA-DR13, 2 patients homozygous for HLA-DR7, and 2 patients expressing HLA-DR7/DR9 were tested.

Figure 2:
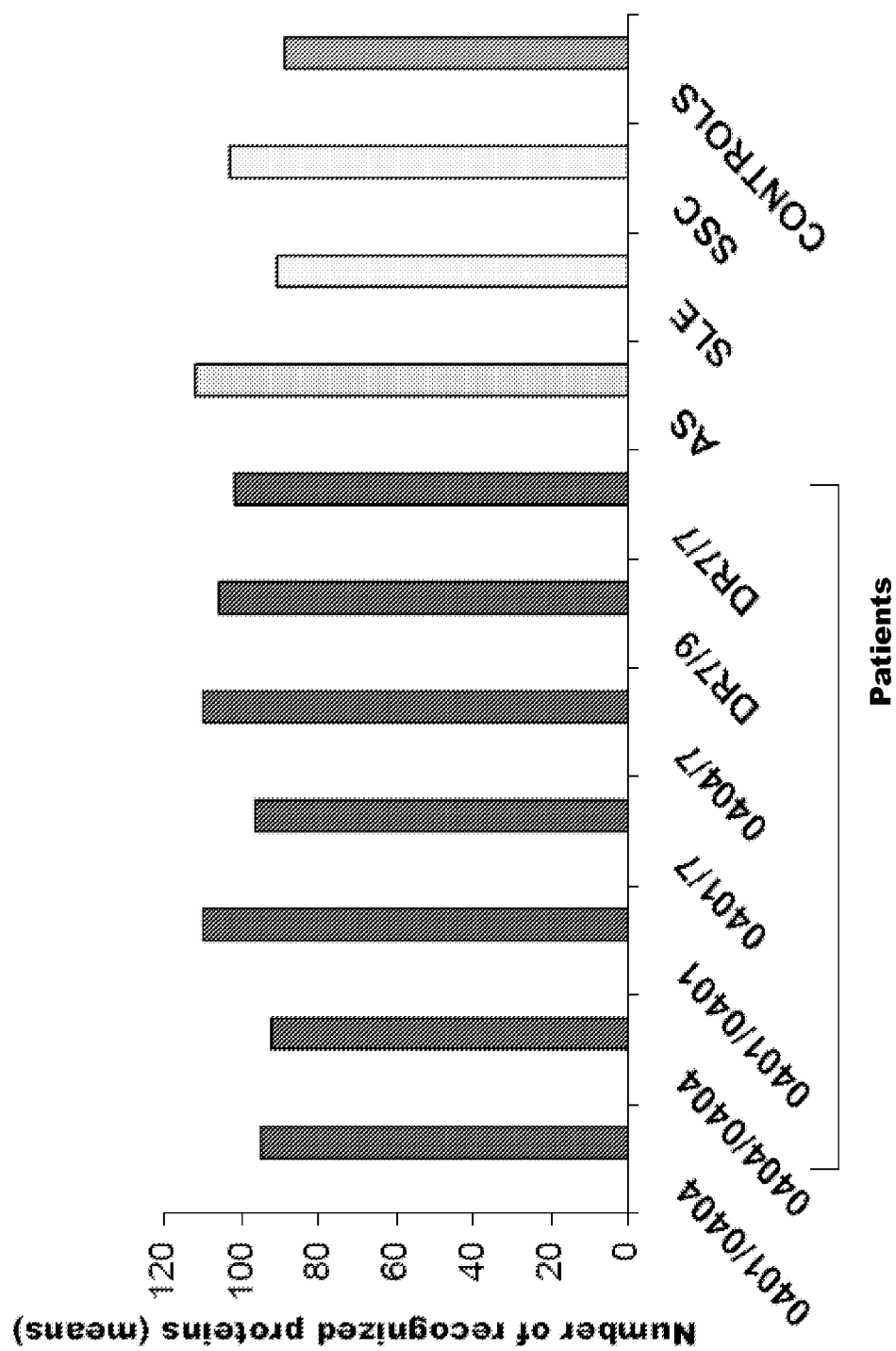
FIG. 2 is a graph showing the mean number of proteins of the ProtoArray Human Protein Microarray that are recognized by AS patients, SLE patients, SSC patients, healthy controls and by RA patients expressing two, one or no RA-associated HLA-DR alleles.

No difference was found in the number of proteins recognized by RA patients expressing two, one or no RA-associated HLA-DR alleles, as shown on FIG. 2 and in the table below.

| Mean number of proteins recognized by RA patients with different HLA-DR genotypes | |
| --- | --- |
| HLA-DR genotype | Number of proteins recognized (mean value) |
| HLA-DRB1*0401/HLA-DRB1*0404 | 95 |
| HLA-DRB1*0404/HLA-DRB1*0404 | 92 |
| HLA-DRB1*0401/HLA-DRB1*0401 | 110 |
| HLA-DRB1*0401/HLA-DRB1*07 | 96 |
| HLA-DRB1*0404/HLA-DRB1*07 | 110 |
| HLA-DR7/DR9 | 106 |

Identification of Specific Antibodies Associated with RA

Figure 3:
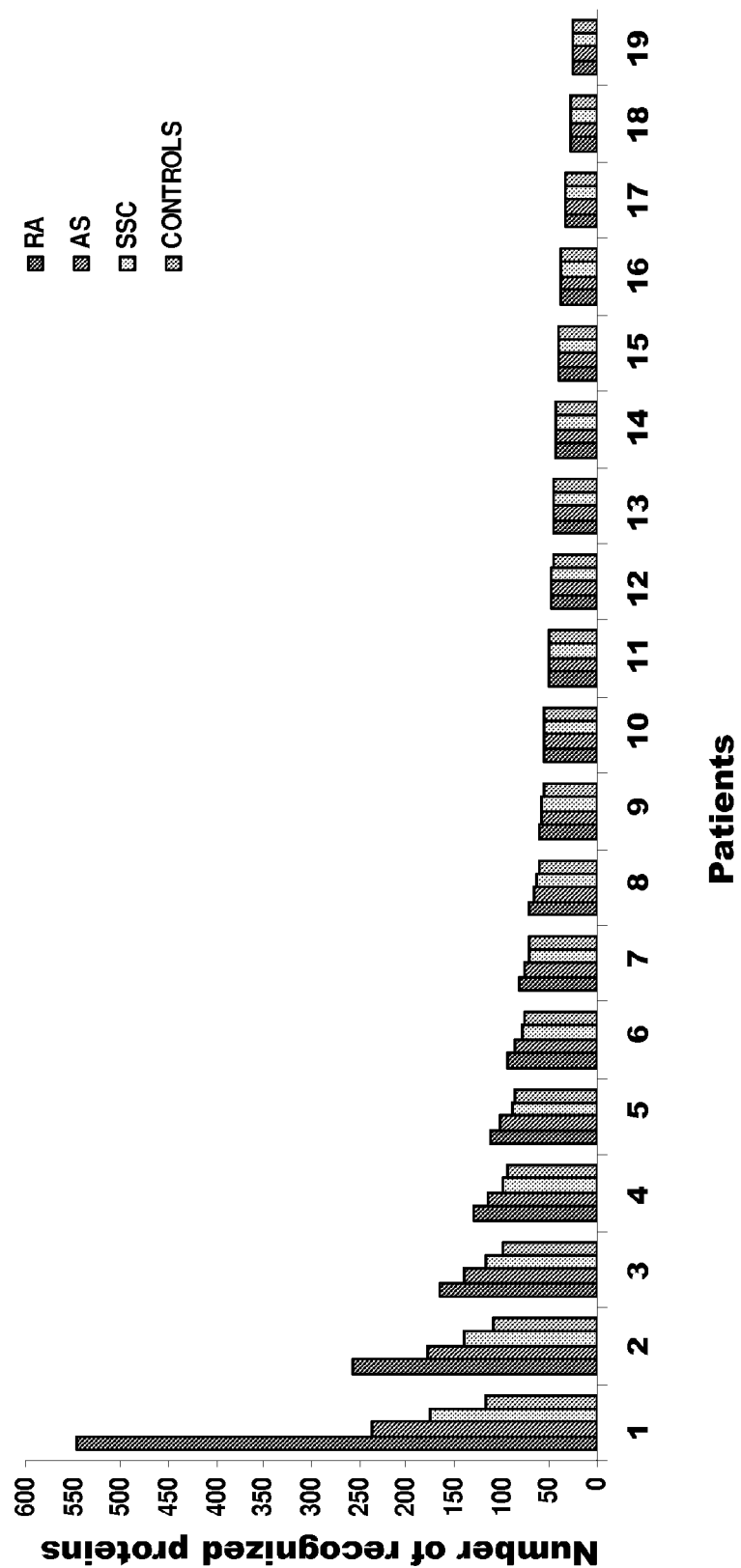
FIG. 3 is a graph showing the total number of proteins of the ProtoArray Human Protein Microarray that are recognized by at least one RA patient, at least two RA patients, at least three RA patients, etc. Also indicated on this graph are the proteins recognized by RA patients that are also recognized by at least 20% of AS patients, at least 20% of SSC patients, and at least 20% of healthy individuals.

FIG. 3 shows the total number of different proteins that are recognized by at least one RA patient, at least 2 RA patients, at least 3 RA patients, etc. Also indicated on FIG. 3 are the proteins recognized by RA patients that are also recognized by at least 20% of AS patients, at least 20% of SSC patients, and at least 20% of healthy individuals. The results presented on this figure demonstrate that many proteins targeted by autoantibodies in the sera of RA patients are not specific of RA but are also reactive with autoantibodies from control groups.

Among the proteins targeted by antoantibodies of the individuals tested, only 3 proteins were found to be specifically recognized by the sera of RA patients and not by the sera of the control groups (FIG. 4). These proteins are PAD4 (peptidyl arginine deiminase 4), PKC beta 1 (protein kinase C beta 1) and PIP4K2C (phosphatylinositol 4 phosphate 5 kinase type II gamma). Among the RA patients tested in the present study, 9/19 were found to be positive for PAD4 versus 0/23 controls (p=0). Similarly, 6/19 RA patients were found to be positive for PCK beta 1 versus 0/23 controls (p=0.014). Finally, 5/19 RA patients were found to be positive for PIPI4K2C versus 0/23 controls (p=0.032).

BRAF catalytic domain (v raf murine sarcoma viral oncogene homolog B1 catalytic domain) is one of the most interesting proteins among the other identified candidate markers for RA. Indeed, 9/19 RA patients tested in this assay were found to be positive for BRAF versus 0/13 disease controls and only 1/10 healthy individuals (p=0.004, 19 patients versus 23 controls).

Autoantigen Validation

To confirm the validity of the protein array detection, the same proteins were tested using different assays.

The frequency of positive sera in patients and controls was determined by ELISA using purified PAD4 and PIP4K2C as immunosorbents. Since, under the conditions used by the Applicants, it was not possible to detect reactivity for PKC beta 1 and BRAF catalytic domain using ELISA assays, a western blotting assay was used instead in the validation of these autoantigen marker candidates.

PAD4. Results from ELISA experiments showed that 29% of RA patients were positive for PAD4 compared to 0% of AS patients and 3% of healthy controls (FIG. 5A). To evaluate the influence of RA-associated HLA-DR alleles on the production of anti-PAD4 antibodies, the frequency of sera positive for PAD4 among groups of patients expressing either two (SE+/SE+), one (SE+/SE−) or no (SE−/SE−) RA-associated HLA-DR alleles was compared. As shown on FIG. 5B, there was no significant difference in the percentage of RA patients positive for PAD4 between patients expressing no RA-associated HLA-DR alleles (SE−/SE−) and patients expressing at least one RA-associated HLA-DR allele (SE+/SE+ and SE+/SE−).

Among SE+/SE+patients, 80% of patients expressing HLA-DRB1*0401/HLA-DRB1*0401 were found to be positive for PAD4 compared to 36% of patients expressing HLA-DRB1*0401/HLA-DRB1*0404, 25% of patients expressing HLA-DRB1*0401/HLA-DRB1*0401, and 17% of patients expressing HLA-DRB1*0404/HLA-DRB1*0404.

These ELISA experiments thus confirmed that PAD4 is a specific autoantigen in RA.

PIP4K2C. Using an ELISA assay, 18% of the RA patients tested were found to be positive for PIP4K2C compared to 18% of AS patients, and 10% of healthy controls (FIG. 6A). Thus, these results do not validate PIPI4K2C as a specific antoantigen in RA.

The percentage of patients positive for PIP4K2C was also calculated for RA patients expressing two, one or no RA-associated HLA-DR alleles. Surprisingly, it was found that a higher percentage of patients expressing two RA-associated HLA-DR alleles are positive for PIP4K2C than RA patients expressing one or no RA-associated HLA-DR allele. Indeed, 40% of SE+/SE+patients were found to be positive for PIP4PK2C versus 5% SE+/SE− patients and 0% SE−/SE− patients.

PKC beta I. Only 2 out of 6 RA patients were found to be positive for PKC beta 1 in western blotting. Based on the partial reactivity observed under the conditions used in this study, PKC beta 1 cannot be validated as a specific autoantigen in RA.

BRAF catalytic domain. Using western blotting, 47% of the 19 RA patients tested in this study were found to be positive for BRAF catalytic domain, while none of the 17 AS patients and none of the 17 healthy controls showed reactivity (FIG. 7A). These results confirm BRAF catalytic domain as a specific autoantigen in RA.

No association was detected between the positivity for BRAF catalytic domain and HLA-DR genotypes in RA patients (FIG. 7B).

Discussion

As already mentioned above, the risk of developing RA is controlled by the two HLA-DR alleles expressed by an individual. HLA-DR alleles can be susceptible, protective or neutral towards the development of RA. Moreover, the 2 HLA-DR alleles expressed by an individual interact. Indeed, two susceptible alleles can cooperate, resulting in a very high risk to develop RA, such as in the HLA-DRB1-0401/0404 genotype, almost exclusively found in patients with RA. This synergistic effect is still unexplained and respective contribution of each allele to the pathogenesis of RA is not understood. In the past, the present Applicants have focused on the extreme synergy between HLA-DRB1*0401 and 0404, and described the original properties for these two alleles. HLA-DRB1*0401 contains a QKRAA motif which, through interaction with the constitutive heat shock protein hsp73, allows extremely good antigen processing (I. Auger et al., Nature Medicine, 1996, 3: 306-310; I. Auger et al., Arthritis and Rheumatism, 2002, 46: 929-933; S. Roth et al., J. Immunol., 2002, 169: 3015-3020). HLA-DRB1-0404 seems to be associated with extremely good antibody production. This is true for anti citrullinated fibrin, anti calpastatin, anti CCP antibodies, and may relate to broad peptide binding properties of HLA-DRB1*0404 (I. Auger et al., Arthritis and Rheumatism, 2005, 52: 3424-3432; I. Auger et al., Annals of Rheumatic Diseases, 2007, 66: 1588-1593; C. Charpin et al., Clin. Exp. Rheumatol., 2008, 26: 627-631).

In order to check whether specific HLA-DR genotypes were associated with specific autoantibody production patterns, the present Applicants have analyzed autoantibodies in the sera of RA patients expressing different HLA-DR genotypes using arrays containing more than 8000 human proteins. They observed that the majority of proteins recognized by RA patients were also found in the sera of controls. No specific autoantibody pattern was found to be associated with particular HLA-DR genotypes. On the other hand, this study has led to the identification of protein markers of RA that can be used in the diagnosis of RA. In particular, the present Applicants have identified and validated two major proteins, BRAF catalytic domain and PAD4, as autoantigen markers.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for the in vitro diagnosis of rheumatoid arthritis in a subject, said method comprising steps of:
   providing an autoantigen marker comprising BRAF catalytic domain, or an antibody-binding fragment thereof, wherein BRAF catalytic domain is of human origin and has an amino acid sequence spanning from amino acid 416 to amino acid 766 of SEQ ID NO: 2;
   contacting a biological sample obtained from the subject with the autoantigen marker for a time and under conditions allowing an antigen-antibody complex to form; and
   detecting the presence or absence of the antigen-antibody complex formed to perform diagnosis,
   wherein the presence of an antigen-antibody complex is indicative of rheumatoid arthritis in the subject.

2. The method of claim 1, wherein the subject is CCP-negative.

3. The method of claim 1, wherein the biological sample is selected from the group consisting of whole blood, serum, plasma, urine, and synovial fluid.

4. The method of claim 1, wherein the autoantigen marker is immobilized on a solid carrier or support.

5. The method of claim 1, wherein detecting the presence or absence of the antigen-antibody complex is by immunoassay.

6. The method of claim 1 further comprising detecting anti-PAD4 antibodies in a biological sample obtained from said subject.

7. The method of claim 1 further comprising measuring, in a biological sample obtained from said subject, the concentration of at least one marker selected from the group consisting of C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, and products of bone, cartilage, or synovium metabolism.

* * * * *